(12) United States Patent
Yamamoto

(10) Patent No.: US 10,842,423 B2
(45) Date of Patent: Nov. 24, 2020

(54) ENDOSCOPE SYSTEM, PROCESSOR DEVICE, AND OPERATION METHOD OF ENDOSCOPE SYSTEM

(71) Applicant: FUJIFILM Corporation, Tokyo (JP)

(72) Inventor: Hiroaki Yamamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 366 days.

(21) Appl. No.: 15/960,562

(22) Filed: Apr. 24, 2018

(65) Prior Publication Data

US 2018/0235527 A1  Aug. 23, 2018

Related U.S. Application Data

(63) Continuation of application No. PCT/JP2016/079388, filed on Oct. 4, 2016.

(30) Foreign Application Priority Data

Dec. 17, 2015 (JP) .................... 2015-246790

(51) Int. Cl.
*A61B 5/1455* (2006.01)
*A61B 1/04* (2006.01)
(Continued)

(52) U.S. Cl.
CPC ........ *A61B 5/14552* (2013.01); *A61B 1/0002* (2013.01); *A61B 1/00009* (2013.01);
(Continued)

(58) Field of Classification Search
CPC ............ A61B 5/14552; A61B 5/14551; A61B 1/00045; A61B 5/14503; A61B 1/04;
(Continued)

(56) References Cited

U.S. PATENT DOCUMENTS

2011/0237882 A1* 9/2011 Saito ................... A61B 5/0084
600/109
2012/0092471 A1 4/2012 Takamatsu
(Continued)

FOREIGN PATENT DOCUMENTS

JP  H03080834  4/1991
JP  2012085720  5/2012
(Continued)

OTHER PUBLICATIONS

"Search Report of Europe Counterpart Application", dated Dec. 6, 2018, p. 1-p. 8.
(Continued)

*Primary Examiner* — Eric F Winakur
*Assistant Examiner* — Abid A Mustansir
(74) *Attorney, Agent, or Firm* — JCIPRNET

(57) ABSTRACT

An endoscope system has an oxygen saturation calculation unit that calculates the oxygen saturation of an observation target using an LUT. The endoscope system includes: an image acquisition unit that acquires a correction image obtained by imaging the observation target before calculating the oxygen saturation; an image correction amount calculation unit that calculates an image correction amount for an oxygen saturation calculation image using the correction image; an image correction unit that corrects the oxygen saturation calculation image according to the image correction amount; and a storage unit that stores the correction image and an oxygen saturation image, which shows the oxygen saturation calculated by the oxygen saturation calculation unit using the oxygen saturation calculation image after correction, so as to be associated with each other.

15 Claims, 18 Drawing Sheets

(51) Int. Cl.
- *A61B 5/145* (2006.01)
- *A61B 1/00* (2006.01)
- *A61B 1/06* (2006.01)
- *A61B 5/00* (2006.01)
- *A61B 8/06* (2006.01)
- *A61B 8/12* (2006.01)
- *A61B 8/08* (2006.01)

(52) U.S. Cl.
CPC ...... *A61B 1/00045* (2013.01); *A61B 1/00057* (2013.01); *A61B 1/00188* (2013.01); *A61B 1/04* (2013.01); *A61B 1/0646* (2013.01); *A61B 1/0684* (2013.01); *A61B 5/14503* (2013.01); *A61B 5/14551* (2013.01); *A61B 1/041* (2013.01); *A61B 5/0071* (2013.01); *A61B 8/06* (2013.01); *A61B 8/12* (2013.01); *A61B 8/488* (2013.01); *A61B 2576/00* (2013.01)

(58) Field of Classification Search
CPC . A61B 1/0684; A61B 1/0646; A61B 1/00188; A61B 1/00057; A61B 1/0002; A61B 1/00009; A61B 5/0071; A61B 2576/00; A61B 8/488; A61B 8/12; A61B 8/06; A61B 1/041
See application file for complete search history.

(56) References Cited

U.S. PATENT DOCUMENTS

| | | | |
|---|---|---|---|
| 2013/0030268 A1 | 1/2013 | Saito | |
| 2014/0187881 A1* | 7/2014 | Saito | A61B 1/0638 600/323 |

FOREIGN PATENT DOCUMENTS

| | | |
|---|---|---|
| JP | 2013022341 | 2/2013 |
| JP | 2014188083 | 10/2014 |
| JP | 2015036055 | 2/2015 |
| WO | 2015025672 | 2/2015 |

OTHER PUBLICATIONS

Office Action of Japan Counterpart Application, with English translation thereof, dated Feb. 19, 2019, pp. 1-5.
"International Search Report (Form PCT/ISA/210)" of PCT/JP2016/079388, dated Dec. 27, 2016, with English translation thereof, pp. 1-3.
"International Preliminary Report on Patentability (Form PCT/IPEA/409) of PCT/JP2016/079388", dated on Aug. 15, 2017, with English translation thereof, pp. 1-15.
Office Action of Japan Counterpart Application, with English translation thereof, dated Sep. 3, 2019, pp. 1-5.

* cited by examiner

ENDOSCOPE SYSTEM, PROCESSOR DEVICE, AND OPERATION METHOD OF ENDOSCOPE SYSTEM

CROSS-REFERENCE TO RELATED APPLICATIONS

This application is a Continuation of PCT International Application No. PCT/JP2016/79388, filed on Oct. 4, 2016, which claims priority under 35 U.S.C. § 119(a) to Japanese Patent Application No. 2015-246790, filed on Dec. 17, 2015. Each of the above application(s) is hereby expressly incorporated by reference, in its entirety, into the present application.

BACKGROUND OF THE INVENTION

1. Field of the Invention

The present invention relates to an endoscope system, a processor device, and an operation method of an endoscope system.

2. Description of the Related Art

In the medical field, it is common to perform diagnosis using an endoscope system including a light source device, an endoscope, and a processor device. In particular, an endoscope system that obtain an image, in which a specific tissue or structure, such as a blood vessel or a gland tube structure, is emphasized, by designing the wavelength of illumination light or performing processing, such as spectral estimation processing, on an image obtained by imaging an observation target as well as observing the observation target naturally has become widespread.

In recent years, there has also been an endoscope system that obtains biological function information using an image obtained by imaging an observation target. For example, diagnosis of a lesion using an image showing the oxygen saturation of hemoglobin (hereinafter, referred to as an oxygen saturation image) contained in the observation target has been performed. In order to calculate the oxygen saturation, the observation target is imaged with illumination light in a wavelength range having different light absorption coefficients for oxygenated hemoglobin and reduced hemoglobin. Then, a predetermined calculation value is calculated using a pixel value of the obtained image, and the oxygen saturation of the observation target is calculated using a look-up table showing a correlation for associating the calculation value with the oxygen saturation. The correlation between the calculation value and the oxygen saturation may differ depending on various parts such as esophagus, stomach, and large intestine, individual differences among patients such as sex and age, and the like. Therefore, in JP2013-22341A, the look-up table is calibrated by performing pre-imaging for imaging a normal part of the observation target before actually calculating the oxygen saturation of the observation target.

SUMMARY OF THE INVENTION

In the case of calibrating a look-up table for associating the calculation value with the oxygen saturation by performing pre-imaging as in JP2013-22341A, it is necessary to appropriately image a normal part of the observation target by the pre-imaging. However, in the pre-imaging, there are a case where the exposure amount is extremely large or small, a case where movement occurs, a case where the observation distance is extremely long or short, and a case where reflection of attached matter or the like occurs. In this case, since it is difficult to accurately calibrate the look-up table, it is difficult to accurately calculate the oxygen saturation. Therefore, since the imaging conditions at the time of pre-imaging greatly influence the oxygen saturation calculation accuracy, it has been required to be able to verify afterward whether or not the pre-imaging has been performed under appropriate conditions.

It is an object of the present invention to provide an endoscope system, a processor device, and an operation method of an endoscope system, which can verify afterward whether or not pre-imaging has been performed under appropriate conditions.

An endoscope system of the present invention comprises: a biometric feature amount calculation unit that calculates a biometric feature amount of an observation target using a plurality of biometric feature amount calculation images obtained by imaging the observation target with a plurality of illumination light beams having different wavelength ranges; an image acquisition unit that acquires a correction image obtained by imaging the observation target; an image correction amount calculation unit that calculates an image correction amount for the biometric feature amount calculation image using the correction image; an image correction unit that corrects the biometric feature amount calculation image according to the image correction amount; and a storage unit that stores the correction image and a first biometric feature amount image, which shows the biometric feature amount calculated by the biometric feature amount calculation unit using the biometric feature amount calculation image after correction, so as to be associated with each other.

The biometric feature amount is a morphological biometric feature amount or a functional biometric feature amount. The morphological biometric feature amount is blood vessel information, and the functional biometric feature amount is an oxygen saturation.

It is preferable that the storage unit stores, in addition to the first biometric feature amount image, any of the biometric feature amount calculation image after correction, the biometric feature amount calculation image before correction, the image correction amount calculated by the image correction amount calculation unit, and the biometric feature amount calculated by the biometric feature amount calculation unit using the biometric feature amount calculation image after correction so as to be associated with the correction image.

It is preferable to further comprise a display unit that displays the correction image and the first biometric feature amount image.

It is preferable to further comprise a region setting unit that sets a usable region for the correction image stored in the storage unit. It is preferable that the image correction amount calculation unit calculates the image correction amount using the usable region in a case where the region setting unit sets the usable region and the image correction unit corrects the biometric feature amount calculation image using the image correction amount calculated by the image correction amount calculation unit using the usable region.

It is preferable that the region setting unit sets a region other than an unused region as the usable region by setting the unused region for the correction image.

It is preferable that the storage unit stores a plurality of sets of the correction images. It is preferable that, in a case where the correction image used for calculation of the image correction amount by the image correction amount calculation unit is not appropriate, the image correction amount calculation unit calculates the image correction amount by changing a set of the correction images and the image correction unit corrects the biometric feature amount calculation image using the image correction amount calculated by changing a set of the correction images by the image correction amount calculation unit.

It is preferable that, in a case where the correction image used for calculation of the image correction amount by the image correction amount calculation unit is not appropriate, the image acquisition unit acquires a new correction image, the image correction amount calculation unit calculates the image correction amount using the new correction image acquired by the image acquisition unit, and the image correction unit corrects the biometric feature amount calculation image using the image correction amount calculated by the image correction amount calculation unit using the new correction image.

It is preferable that, between a case where the image acquisition unit acquires the correction image and the biometric feature amount calculation image in real time during observation of the observation target and a case where the image acquisition unit acquires the correction image and the biometric feature amount calculation image after completion of observation of the observation target, the image correction amount calculation unit changes calculation accuracy of the image correction amount, and the image correction unit changes correction accuracy of the biometric feature amount calculation image.

It is preferable that calculation accuracy of the image correction amount and correction accuracy of the biometric feature amount calculation image in a case where the image acquisition unit acquires the correction image and the biometric feature amount calculation image after completion of observation of the observation target are higher than calculation accuracy of the image correction amount and correction accuracy of the biometric feature amount calculation image in a case where the image acquisition unit acquires the correction image and the biometric feature amount calculation image in real time during observation of the observation target.

It is preferable that the image acquisition unit acquires the correction image, which is obtained by imaging the observation target, before calculating the biometric feature amount by the biometric feature amount calculation unit.

An endoscope system of the present invention comprises: a biometric feature amount calculation unit that calculates a biometric feature amount of an observation target using a plurality of biometric feature amount calculation images, which are obtained by imaging the observation target with a plurality of illumination light beams having different wavelength ranges, and a look-up table for associating pixel values of the biometric feature amount calculation images with the biometric feature amount of the observation target; an image acquisition unit that acquires a correction image obtained by imaging the observation target; a table calibration unit that calibrates the look-up table using the correction image; and a storage unit that stores the correction image and a second biometric feature amount image, which shows the biometric feature amount calculated by the biometric feature amount calculation unit using the look-up table after calibration, so as to be associated with each other.

A processor device of the present invention comprises: a biometric feature amount calculation unit that calculates a biometric feature amount of an observation target using a plurality of biometric feature amount calculation images obtained by imaging the observation target with a plurality of illumination light beams having different wavelength ranges; an image acquisition unit that acquires a correction image obtained by imaging the observation target; an image correction amount calculation unit that calculates an image correction amount for the biometric feature amount calculation image using the correction image; an image correction unit that corrects the biometric feature amount calculation image according to the image correction amount; and a storage unit that stores the correction image and a first biometric feature amount image, which shows the biometric feature amount calculated by the biometric feature amount calculation unit using the biometric feature amount calculation image after correction, so as to be associated with each other.

An operation method of an endoscope system of the present invention is an operation method of an endoscope system having a biometric feature amount calculation unit that calculates a biometric feature amount of an observation target using a plurality of biometric feature amount calculation images obtained by imaging the observation target with a plurality of illumination light beams having different wavelength ranges. The operation method of an endoscope system comprises: a step in which an image acquisition unit acquires a correction image obtained by imaging the observation target; a step in which an image correction amount calculation unit calculates an image correction amount for the biometric feature amount calculation image using the correction image; a step in which an image correction unit corrects the biometric feature amount calculation image according to the image correction amount; a step in which the biometric feature amount calculation unit calculates the biometric feature amount using the biometric feature amount calculation image after correction; and a step in which a storage unit stores the correction image and a first biometric feature amount image, which shows the biometric feature amount calculated by the biometric feature amount calculation unit using the biometric feature amount calculation image after correction, so as to be associated with each other.

According to the endoscope system, the processor device, and the operation method of an endoscope system of the present invention, it is possible to verify afterward whether or not pre-imaging has been performed under appropriate conditions.

DESCRIPTION OF THE PREFERRED EMBODIMENTS

First Embodiment

Figure 1:
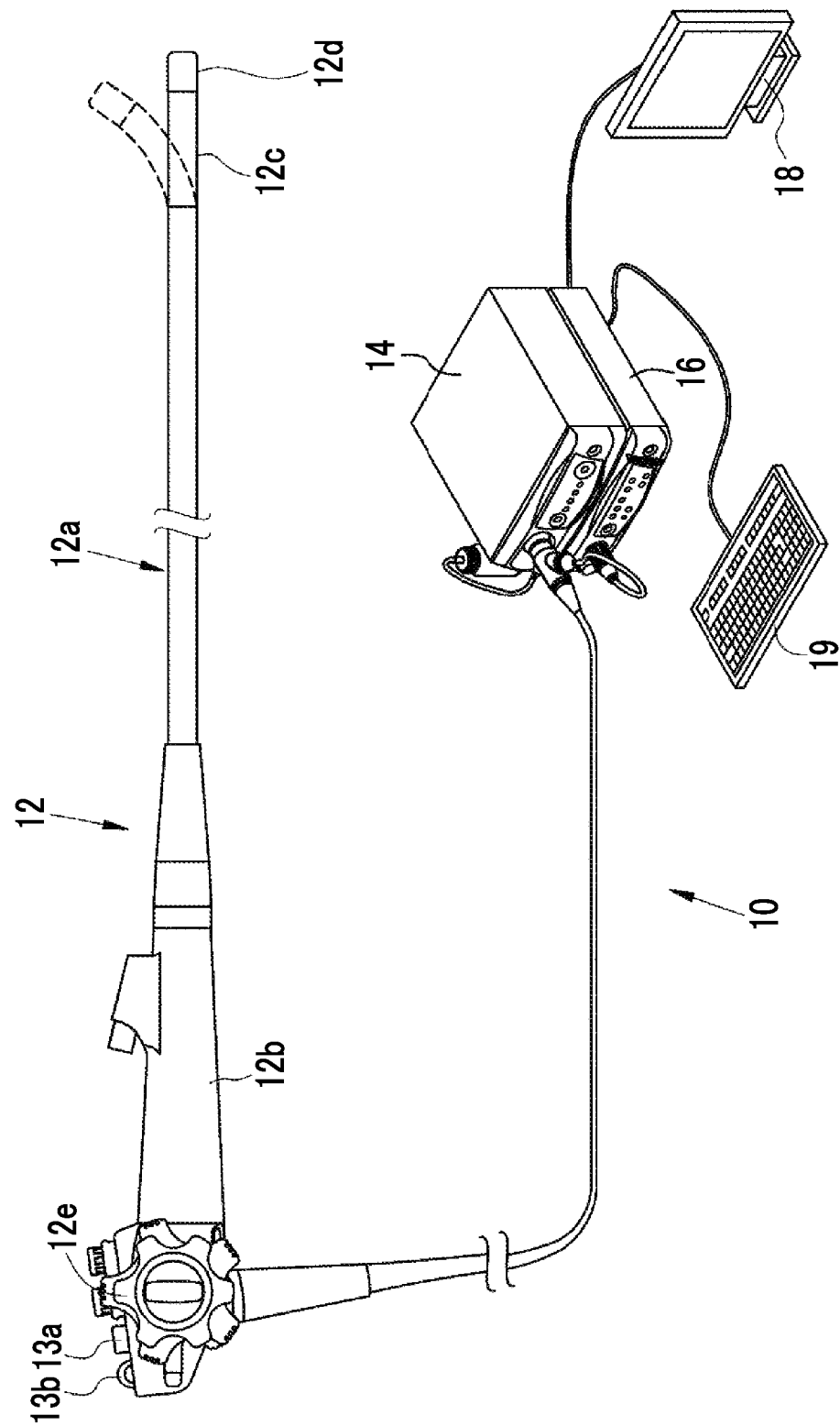
FIG. 1 is an external view of an endoscope system.

As shown in FIG. 1, an endoscope system 10 has an endoscope 12, a light source device 14, a processor device 16, a monitor 18 (display unit), and a console 19. The endoscope 12 is optically connected to the light source device 14, and is electrically connected to the processor device 16. The endoscope 12 has an insertion part 12a that is inserted into a subject, an operation unit 12b provided in a proximal end portion of the insertion part 12a, and a bending portion 12c and a distal end portion 12d that are provided at the distal end side of the insertion part 12a. By operating an angle knob 12e of the operation unit 12b, the bending portion 12c is bent. Through the bending operation, the distal end portion 12d is directed in a desired direction.

In addition to the angle knob 12e, a mode selector switch 13a and a zoom operation unit 13b are provided in the operation unit 12b. The mode selector switch 13a is used for an observation mode switching operation. The endoscope system 10 has two observation modes of a normal observation mode and an oxygen saturation observation mode. In the normal observation mode, the observation target is imaged by illuminating the observation target with white light, and an image having a natural color tone (hereinafter, referred to as a normal image) is displayed on the monitor 18. In the oxygen saturation observation mode, the oxygen saturation of the observation target is calculated by using a correlation between an image, which is obtained by imaging the observation target by illuminating the observation target with light in a wavelength range having different light absorption coefficients for oxygenated hemoglobin and reduced hemoglobin, and an oxygen saturation as a biometric feature amount, and an oxygen saturation image showing the oxygen saturation is displayed on the monitor 18. The biometric feature amount indicates, for example, information indicating a form, such as a size or a shape of a blood vessel or a pit pattern, or information indicating a function, such as the action or metabolism of an observed part. The former biometric feature amount is also referred to as a morphological biometric feature amount, and the latter biometric feature amount is also referred to as a functional biometric feature amount. The oxygen saturation is included in the functional biometric feature amount.

The processor device 16 is electrically connected to the monitor 18 and the console 19. The monitor 18 outputs and displays an image, image information to be attached to the image, or the like in each observation mode. The console 19 functions as a user interface for receiving an input operation, such as a function setting. In addition, an external recording unit (not shown) in which an image, image information, or the like is recorded may be connected to the processor device 16.

Figure 2:
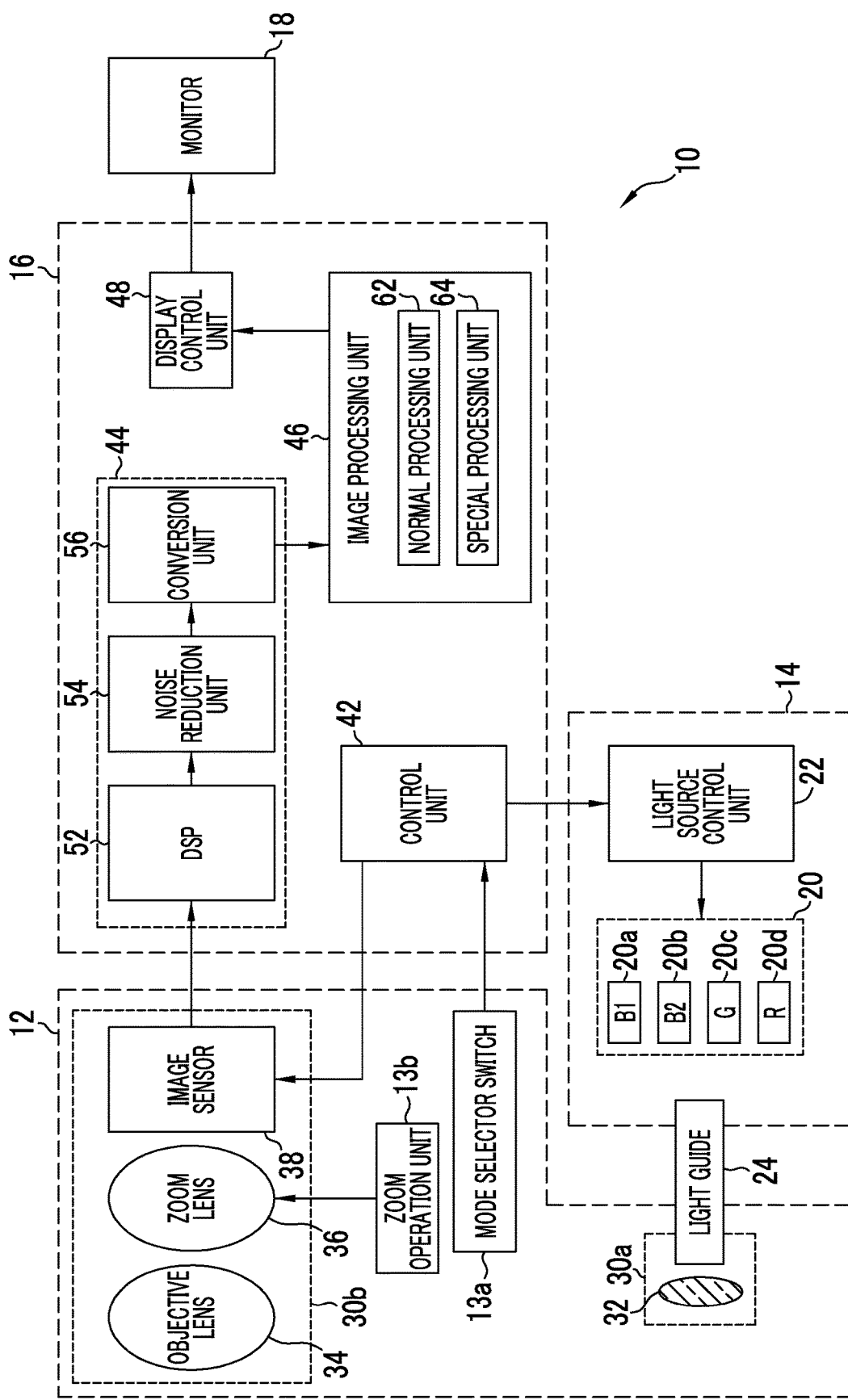
FIG. 2 is a block diagram of the endoscope system.

As shown in FIG. 2, the light source device 14 includes a light source unit 20 that emits illumination light and a light source control unit 22 that controls the driving of the light source unit 20.

The light source unit 20 includes four light sources of a B1 light source 20a, a B2 light source 20b, a G light source 20c, and an R light source 20d. In the present embodiment, the B1 light source 20a, the B2 light source 20b, the G light source 20c, and the R light source 20d are all light emitting diodes (LEDs). Instead of these LEDs, a combination of a laser diode (LD), a phosphor, and a band limiting filter, a combination of a broadband light source such as a xenon lamp and a band limiting filter, and the like can be used as the light source unit 20.

Both the B1 light source 20a and the B2 light source 20b are blue light sources that emit blue light. However, the center wavelength and the wavelength range are different between blue light emitted by the B1 light source 20a (hereinafter, referred to as B1 light) and blue light emitted by the B2 light source 20b (hereinafter, referred to as B2 light). The B1 light is narrowband blue light having a center wavelength and a wavelength range of 470±10 nm. The center wavelength and the wavelength range of the B1 light are a center wavelength and a wavelength range at which the difference between the light absorption coefficients of oxygenated hemoglobin and reduced hemoglobin in the blue wavelength range is substantially maximized. Therefore, the B1 light is used in the oxygen saturation observation mode. On the other hand, the B2 light is broadband blue light having a center wavelength of about 450±10 nm and a wavelength range of about 400 to 500 nm. The B2 light is used in the normal observation mode and the oxygen saturation observation mode.

The G light source 20c is a green light source that emits broadband green light (hereinafter, referred to as G light) having a center wavelength of 540±20 nm and a wavelength range of about 480 to 600 nm. The R light source 20d is a red light source that emits broadband red light (hereinafter, referred to as R light) having a center wavelength of 640±20 nm and a wavelength range of about 600 to 700 nm. The G light and the R light are used in the normal observation mode and the oxygen saturation observation mode. The center wavelengths and the peak wavelengths of light beams of the respective colors may be the same or different.

The light source control unit 22 controls the spectrum or the amount of illumination light by controlling the ON and OFF timing, the light emission amount, and the like of each of the light sources 20a to 20d forming the light source unit 20.

In the case of the normal observation mode, the light source control unit 22 turns on the B2 light source 20b, the G light source 20c, and the R light source 20d. Therefore, in the normal observation mode, white light configured to include the B2 light, the G light, and the R light is illumination light.

In the case of the oxygen saturation observation mode, the light source control unit 22 switches illumination light for each imaging frame. Specifically, the B1 light source 20a is turned on in a certain imaging frame (hereinafter, referred to as a first frame), and the B2 light source 20b, the G light source 20c, and the R light source 20d are turned on in the next imaging frame (hereinafter, referred to as a second frame). That is, illumination light of the first frame is the B1 light, and illumination light of the second frame is white light configured to include the B2 light, the G light, and the R light.

In the case of shifting from the normal observation mode to the oxygen saturation observation mode, the light source control unit 22 sequentially turns on the B1 light source 20a, the B2 light source 20b, the G light source 20c, and the R light source 20d in accordance with the imaging frame, and sequentially switches the illumination light to B1 light, the B2 light, the G light, and the R light. Switching between various illumination light beams is performed at least once in the case of shifting from the normal observation mode to the oxygen saturation observation mode. This is for correction of the oxygen saturation, which will be described later.

The various illumination light beams described above that are emitted from the light source unit 20 are incident on a light guide 24. The light guide 24 is built into the endoscope 12 and a universal cord (cord for connecting the endoscope 12 to the light source device 14 and the processor device 16), and makes the illumination light propagate to the distal end portion 12d of the endoscope 12. As the light guide 24, it is possible to use a multi-mode fiber. As an example, it is possible to use a small-diameter fiber cable having a core diameter of 105 μm, a cladding diameter of 125 μm, and a diameter of ϕ0.3 mm to μ0.5 mm in a case where a protective layer as an outer skin is included.

An illumination optical system 30a and an imaging optical system 30b are provided in the distal end portion 12d of the endoscope 12. The illumination optical system 30a has an illumination lens 32, and illumination light is emitted to the observation target through the illumination lens 32. The imaging optical system 30b has an objective lens 34, a zoom lens 36, and an image sensor 38. The image sensor 38 images the observation target using reflected light, scattered light, and the like (including fluorescence emitted from the observation target or fluorescence due to medicine administered to the observation target) of the illumination light returning from the observation target through the objective lens 34 and the zoom lens 36. The zoom lens 36 is moved by operating the zoom operation unit 13b, thereby enlarging or reducing the observation target imaged by using the image sensor 38.

The image sensor 38 is a primary color system color sensor, and has three kinds of pixels of a blue pixel (B pixel) in which a blue color filter is provided, a green pixel (G pixel) in which a green color filter is provided, and a red pixel (R pixel) in which a red color filter is provided. Therefore, in the case of imaging the observation target with the image sensor 38, three kinds of images of a blue image (B image), a green image (G image), and a red image (R image) are obtained.

Although the image sensor 38 is a primary color system color sensor, it is also possible to use a complementary color system color sensor. For example, the complementary color system color sensor has a cyan pixel in which a cyan color filter is provided, a magenta pixel in which a magenta color filter is provided, a yellow pixel in which a yellow color filter is provided, and a green pixel in which a green color filter is provided. Images of the respective colors obtained in the case of using the complementary color system color sensor can be converted into the same B image, G image, and R image as in the case of using the primary color system color sensor.

In the case of the oxygen saturation observation mode, since the illumination light of the first frame is the B1 light and includes neither green light nor red light, only the B image is substantially obtained in the first frame of the oxygen saturation observation mode. On the other hand, since the illumination light of the second frame of the oxygen saturation observation mode is white light, a B image, a G image, and an R image are obtained. Hereinafter, for the sake of distinction, the B image obtained in the first frame is referred to as a B1 image, and the B image obtained in the second frame is referred to as a B2 image.

In the oxygen saturation observation mode, in addition to performing "main imaging" in which the oxygen saturation of the observation target is actually calculated as described above to obtain an oxygen saturation calculation image that is used in generating an oxygen saturation image, "pre-imaging" for obtaining a correction image to be used for correction of the oxygen saturation is performed.

Since the pre-imaging is imaging performed to correct the oxygen saturation, a normal part of the observation target is imaged. The normal part of the observation target is a part considered that there is no obvious lesion, attached matter, and the like and no abnormality occurs in oxygen saturation. Hereinafter, the B1 image, the B2 image, the G image, and the R image obtained by performing the main imaging of a part where the oxygen saturation is to be actually calculated are referred to as an oxygen saturation calculation image 76 (refer to FIG. 3). In addition, the B1 image, the B2 image, the G image, and the R image obtained by performing the pre-imaging of a normal part of the observation target for correction are referred to as a correction image 86 (refer to FIG. 3). In the present embodiment, in the case of shifting from the normal observation mode to the oxygen saturation observation mode, pre-imaging is performed once before the main imaging. In a case where pre-imaging is performed once, images of four frames (B1 image, B2 image, G image, and R image) are obtained as described above. The pre-imaging may be performed after the main imaging. For one pre-imaging, the main imaging may be performed once or may be performed multiple times. The pre-imaging may also be performed twice or more. The pre-imaging may be performed by an input operation on the console 19 or the like.

The processor device 16 includes a control unit 42, an image acquisition unit 44, an image processing unit 46, and a display control unit 48. The control unit 42 switches the observation mode by controlling the light source control unit 22 and the image sensor 38 in response to an input of a mode switching signal from the mode selector switch 13a. Specifically, the control unit 42 performs designation of the type or the amount of illumination light for the light source control unit 22, control of the length of the exposure time of the image sensor 38, a gain at the time of image output, and the like, synchronous control of the switching timing of the imaging frame and illumination light, and the like. For example, the processor device 16 has a central processing unit (CPU), and the CPU functions as the control unit 42, the image acquisition unit 44, the image processing unit 46, and the display control unit 48.

The image acquisition unit 44 acquires an image of each color from the image sensor 38. In the case of the normal observation mode, the B image, the G image, and the R image are acquired from the image sensor 38. In the case of the oxygen saturation observation mode, the B1 image is acquired in the first frame, and the B2 image, the G image, and the R image are acquired in the second frame. In the case of shifting from the normal observation mode to the oxygen saturation observation mode, the B1 image, the B2 image, the G image, and the R image are sequentially acquired frame by frame. The image acquisition unit 44 has a digital signal processor (DSP) 52, a noise reduction unit 54, and a conversion unit 56, and performs various kinds of processing on the acquired images using these units.

The DSP 52 performs various kinds of processing, such as defect correction processing, offset processing, gain correction processing, linear matrix processing, gamma conversion processing, demosaic processing, and YC conversion processing, on the acquired images.

The defect correction processing is processing for correcting the pixel value of each pixel corresponding to the defective pixel of the image sensor 38. The offset processing is processing for setting an accurate zero level by removing a dark current component from the image subjected to the defect correction processing. The gain correction processing is processing for adjusting the signal level of each image by multiplying the image subjected to the offset processing by the gain. The linear matrix processing is processing for enhancing the color reproducibility of the image subjected to the offset processing. The gamma conversion processing is processing for adjusting the brightness or saturation of the image subjected to the linear matrix processing. The demosaic processing (also referred to as isotropic processing or simultaneous processing) is processing for interpolating the pixel values of missing pixels, and is performed on the image after the gamma conversion processing. The missing pixel is a pixel having no pixel value because pixels of other colors are arranged in the image sensor 38. For example, since the B image is an image obtained from the B pixel, a pixel at a position corresponding to the G or R pixel of the image sensor 38 has no pixel value. In the demosaic processing, the pixel values of pixels at the positions of the G and R pixels of the image sensor 38 are generated by interpolating the B image. The YC conversion processing is processing for converting the image subjected to the demosaic processing into a brightness image Y, a color difference image Cb, and a color difference image Cr.

The noise reduction unit 54 performs noise reduction processing on the brightness image Y, the color difference image Cb, and the color difference image Cr using, for example, a moving average method or a median filter method. The conversion unit 56 reconverts the brightness image Y, the color difference image Cb, and the color difference image Cr after the noise reduction processing into images of the respective colors of BGR.

The image processing unit 46 has a normal processing unit 62 and a special processing unit 64. The normal processing unit 62 operates in the normal observation mode, and generates a normal image by performing color conversion processing, color emphasis processing, and structure emphasis processing on the images of the respective colors of BGR. In the color conversion processing, 3×3 matrix processing, gradation conversion processing, three-dimensional look-up table (LUT) processing, and the like are performed on the images of the respective colors of BGR. The color emphasis processing is processing for emphasizing the color of the image, and the structure emphasis processing is processing for emphasizing the structure of the observation target, such as a blood vessel or a pit pattern, for example. The display control unit 48 converts the normal image acquired from the normal processing unit 62 into a format suitable for display, and inputs the normal image to the monitor 18. As a result, the normal image is displayed on the monitor 18.

Figure 3:
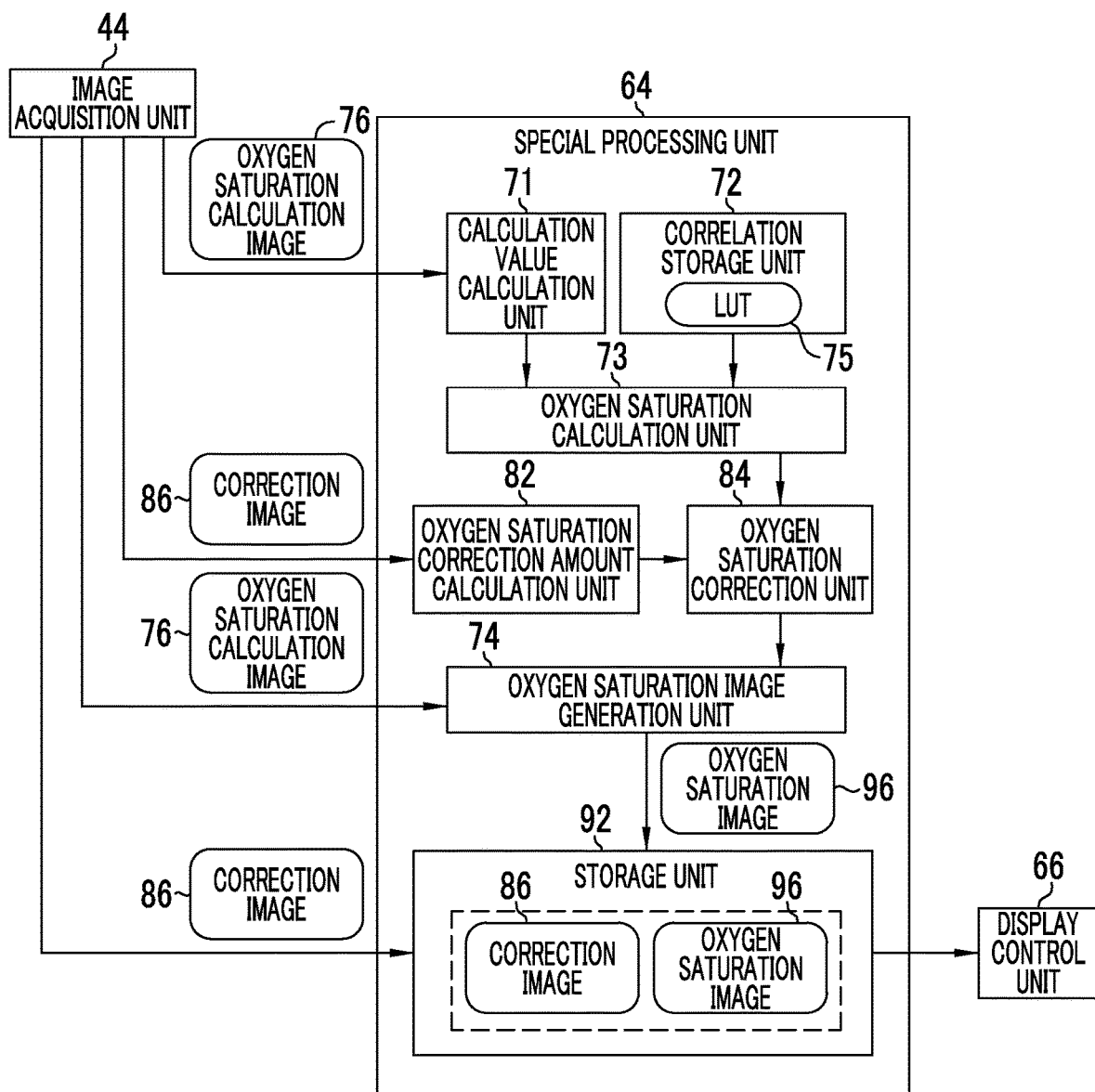
FIG. 3 is a block diagram of a special processing unit.

The special processing unit 64 operates in the oxygen saturation observation mode, and calculates the oxygen saturation of the observation target using the oxygen saturation calculation image and generates an oxygen saturation image. As shown in FIG. 3, the special processing unit 64 includes a calculation value calculation unit 71, a correlation storage unit 72, an oxygen saturation calculation unit 73, and an oxygen saturation image generation unit 74.

The calculation value calculation unit 71 acquires the oxygen saturation calculation image 76 from the image acquisition unit 44, and calculates a calculation value, which is used for calculation of the oxygen saturation, by calculation using the pixel value of the oxygen saturation calculation image 76. Specifically, the calculation value calculation unit 71 calculates a ratio B1/G between the B1 image and the G image and a ratio R/G between the R image and the G image for each pixel. The ratio B1/G and the ratio R/G are calculation values calculated by the calculation value calculation unit 71, and are calculation results of arithmetic operations using the pixel values of the image acquired by the image acquisition unit 44. The ratio B1/G mainly depends on the oxygen saturation and the blood volume, and the ratio R/G mainly depends on the blood volume. Therefore, by observing the balance between the ratio B1/G and the ratio R/G, it is possible to calculate the oxygen saturation of the observation target excluding the dependency on the blood volume.

Figure 4:
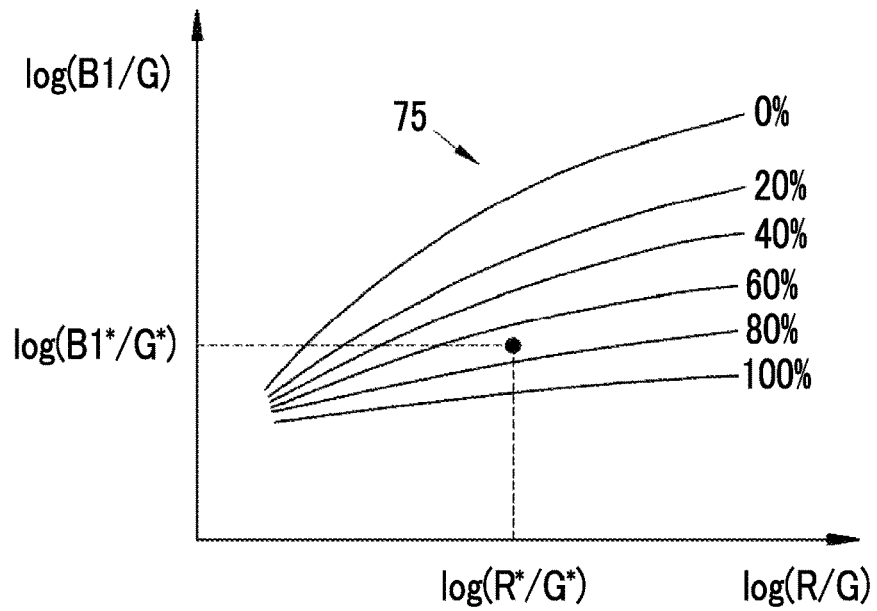
FIG. 4 is a graph showing the content of an LUT used for the calculation of the oxygen saturation.

The correlation storage unit 72 stores a correlation, which is obtained by associating the ratio B1/G and the ratio R/G that are the calculation result of the calculation value calculation unit 71 with the oxygen saturation, in a look-up table (LUT) 75. As shown in FIG. 4, the correlation stored in an LUT 75 is a two-dimensional table in which isolines of oxygen saturation are defined in a two-dimensional space having the ratio B1/G and the ratio R/G as axes. The position and shape of each isoline for the ratio B1/G and the ratio R/G are obtained in advance by physical simulation of light scattering. The correlation storage unit 72 stores the correlation between the ratio B1/G and the ratio R/G and the oxygen saturation, for example, in a log scale.

The oxygen saturation calculation unit 73 calculates an oxygen saturation corresponding to the ratio B1/G and the ratio R/G calculated by the calculation value calculation unit 71 with reference to the LUT 75 stored in the correlation storage unit 72. For example, in a case where the value of the ratio B1/G in a specific pixel is B1*/G* and the value of the ratio R/G is R*/G*, the oxygen saturation corresponding to these values is "70%" in a case where the LUT 75 is referred to (refer to FIG. 4). Therefore, the oxygen saturation calculation unit 73 calculates the oxygen saturation of the specific pixel as "70%".

The ratio B1/G and the ratio R/G hardly become very large values, or conversely, hardly become very small values. That is, the combination of the ratio B1/G and the ratio R/G hardly becomes a combination exceeding the upper limit isoline indicating the oxygen saturation of "100%", or hardly becomes a combination less than the lower limit isoline indicating the oxygen saturation of "0%". For example, the oxygen saturation calculation unit 73 sets the oxygen saturation to 100% in a case where the oxygen saturation exceeds 100%, and sets the oxygen saturation to 0% in a case where the oxygen saturation is less than 0%.

The oxygen saturation image generation unit 74 generates an oxygen saturation image using the oxygen saturation calculation image 76 and the oxygen saturation calculated by the oxygen saturation calculation unit 73. Specifically, the oxygen saturation image generation unit 74 generates an image as a base of the oxygen saturation image (hereinafter, referred to as a base image) using the B2 image, the G image, and the R image obtained in the second frame of the oxygen saturation calculation image 76. The base image is generated by performing color conversion processing, color emphasis processing, and structure emphasis processing on the B2 image, the G image, and the R image. That is, the base image is a normal image generated using images obtained in the second frame of the oxygen saturation observation mode. In a case where the base image is generated, the oxygen saturation image generation unit 74 colors the base image using the oxygen saturation calculated by the oxygen saturation calculation unit 73, thereby generating an oxygen saturation image showing the oxygen saturation by color.

In a case where the oxygen saturation is calculated using the oxygen saturation calculation image 76 in the oxygen saturation observation mode as described above, the special processing unit 64 corrects the oxygen saturation. Therefore, the special processing unit 64 includes an oxygen saturation correction amount calculation unit 82 and an oxygen saturation correction unit 84 in addition to each unit described above (refer to FIG. 3).

The oxygen saturation correction amount calculation unit 82 calculates an oxygen saturation correction amount. Specifically, the oxygen saturation correction amount calculation unit 82 acquires the correction image 86 from the image acquisition unit 44, and calculates an oxygen saturation correction amount for correcting the value of the oxygen saturation calculated by the oxygen saturation calculation unit 73 using the correction image 86. More specifically, the oxygen saturation correction amount calculation unit 82 calculates the ratio B1/G and the ratio R/G for each pixel using the B1 image, the G image, and the R image of the correction image 86, and calculates representative values of the calculated ratios B1/G and R/G. Then, an oxygen saturation corresponding to the representative values of the ratio B1/G and the ratio R/G is calculated with reference to the LUT 75. In the present embodiment, the representative values of the ratio B1/G and the ratio R/G are average values. However, other statistics, such as a median value and a mode value, can be used as representative values.

Figure 5:
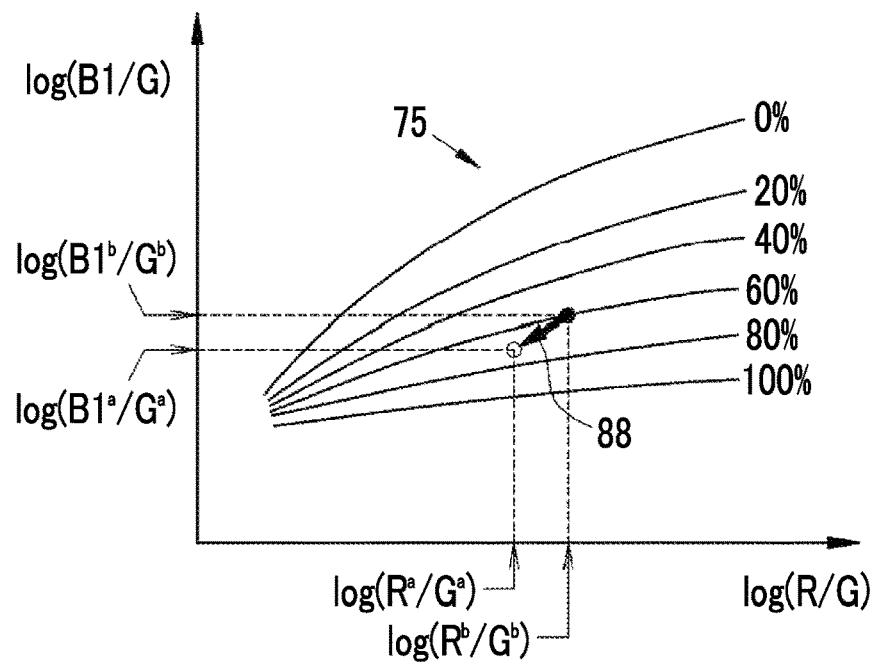
FIG. 5 is a graph showing a deviation between an ideal observation target and an actual observation target.

For example, as shown in FIG. 5, it is assumed that a representative value of the ratio B1/G calculated using an image obtained by imaging a normal part of an ideal observation target is $B1^a/G^a$ and a representative value of the ratio R/G is $R^a/G^a$. In addition, it is assumed that a representative value of the ratio B1/G calculated using the actual correction image 86 is $B1^b/G^b$ and a representative value of the ratio R/G calculated using the actual correction image 86 is $R^b/G^b$. In FIG. 5, the oxygen saturation corresponding to $B1^a/G^a$ and $R^a/G^a$ is 70%, and the oxygen saturation corresponding to $B1^b/G^b$ and $R^b/G^b$ is 60%.

The oxygen saturation correction amount calculation unit 82 calculates an oxygen saturation correction amount 88 with respect to the oxygen saturation calculated by the oxygen saturation calculation unit 73 from the relationship between the oxygen saturation (70%), which is a reference in a case where an image obtained by imaging the normal part of the ideal observation target is used, and the oxygen saturation (60%) calculated using the actual correction image 86. In the present embodiment, the oxygen saturation correction amount 88 is, for example, "+10%".

In a case where the oxygen saturation calculation unit 73 calculates the oxygen saturation, the oxygen saturation correction unit 84 corrects the value of the oxygen saturation. Specifically, the oxygen saturation correction unit 84 performs the correction according to the oxygen saturation correction amount 88 calculated by the oxygen saturation correction amount calculation unit 82. For example, in a case where the oxygen saturation calculation unit 73 calculates the oxygen saturation of a certain pixel as "50%" using the oxygen saturation calculation image 76, the oxygen saturation correction unit 84 corrects the value (50%) of the oxygen saturation according to the above oxygen saturation correction amount 88 (+10%) so that the oxygen saturation of "60% (=50%+10%)" is obtained.

The oxygen saturation image generation unit 74 generates a base image using the oxygen saturation calculation image 76, and generates an oxygen saturation image by coloring the generated base image using the oxygen saturation. However, in the present embodiment, the oxygen saturation image generation unit 74 does not use the oxygen saturation calculated by the oxygen saturation calculation unit 73 as it is, but uses the oxygen saturation corrected by the oxygen saturation correction unit 84.

The oxygen saturation correction unit 84 can correctly correct the oxygen saturation in a case where the correction image 86 is an image obtained by appropriately imaging the normal part of the observation target. However, even in a case where the normal part of the observation target is imaged, the oxygen saturation cannot be correctly corrected depending on the imaging conditions in some cases. For example, in a case where the observation distance is not appropriate, the correction image 86 may be too dark since the amount of light is insufficient. Conversely, the correction image 86 may be too bright since the amount of light is too large. As described above, in a case where the brightness of the correction image 86 is not appropriate, the calculation of the oxygen saturation correction amount and the correction of the oxygen saturation by the oxygen saturation correction unit 84 may be inaccurate.

In addition, even in a case where the movement of the observation target is large, a case where residues, residual liquid, or the like adheres to the observation target, a case where the relative distance between the endoscope and the observation target (hereinafter, referred to as an observation distance) is extremely short or long, the calculation of the oxygen saturation correction amount by the oxygen saturation correction amount calculation unit 82 and the correction of the oxygen saturation by the oxygen saturation correction unit 84 may be inaccurate. In a case where the calculation of the oxygen saturation correction amount and the correction of the oxygen saturation are inaccurate, there is a high possibility that the oxygen saturation image does not accurately show the oxygen saturation of the observation target. For this reason, the oxygen saturation image cannot be trusted as an image used in a case where the doctor desires to check the image again after the diagnosis or desires to perform minute observation.

Therefore, in addition to the oxygen saturation correction amount calculation unit 82 and the oxygen saturation correction unit 84 described above, the special processing unit 64 includes a storage unit 92 that stores images so that the doctor can check the images afterward after the diagnosis.

The storage unit 92 stores the correction image 86 used for correction of the oxygen saturation and the oxygen saturation image so as to be associated with each other. The correction image 86 and the oxygen saturation image are stored in the storage unit 92 after being compressed by an image compression processing unit (not shown). Here, since the correction image 86 is used for later check after the diagnosis in a verification mode to be described later, it is required to store the correction image 86 in the storage unit 92 while suppressing the reduction in resolution due to compression. On the other hand, since the oxygen saturation image is sequentially generated by the oxygen saturation image generation unit 74, it is required to store the oxygen saturation image in the storage unit 92 with a reduced file capacity. Therefore, in the present embodiment, the compression ratio of the oxygen saturation image is set to be higher than the compression ratio of the correction image 86. The file format of the oxygen saturation image stored in the storage unit 92 is, for example, a joint photographic experts group (JPEG) format. The file format of the correction image 86 stored in the storage unit 92 is, for example, a bitmap format. The file format is not limited to the above formats.

The storage unit 92 assigns the same file name (for example, date) to the correction image 86 and the oxygen saturation image having different file formats as described above. As a result, the correction image 86 and the oxygen saturation image having the same file name and different extensions are stored in the storage unit 92 so as to be associated with each other.

For example, in a case where one main imaging is performed for one pre-imaging, the storage unit 92 stores the correction image 86 obtained by one pre-imaging and the oxygen saturation image obtained by one main imaging so as to be associated with each other. In a case where a plurality of oxygen saturation images are obtained for the correction image 86 obtained by one pre-imaging by performing the main imaging multiple times for one pre-imaging, the storage unit 92 may store each oxygen saturation image so as to be associated with the correction image 86 obtained by one pre-imaging.

In the case of the oxygen saturation observation mode, the display control unit 48 converts the oxygen saturation image generated by the oxygen saturation image generation unit 74 into a format suitable for display and inputs the oxygen saturation image to the monitor 18. As a result, an oxygen saturation image 96 is displayed on the monitor 18, as shown in (a) of FIG. 6. In the case of displaying the oxygen saturation image 96 on the monitor 18, the display control unit 48 displays a color scale 97 indicating the correspondence between the color and the height of the oxygen saturation on the monitor 18.

By displaying the oxygen saturation image 96 on the monitor 18, the doctor can perform diagnosis while observing the oxygen saturation image 96 displayed on the monitor 18. However, in a case where pre-imaging is not performed under appropriate conditions, the correction image 86 that is not appropriate as an image used for the calculation of the oxygen saturation correction amount and the correction of the oxygen saturation may be acquired. In this case, since the oxygen saturation image that does not accurately show the oxygen saturation of the observation target is displayed, inaccurate information may be provided to the doctor.

Figure 6:
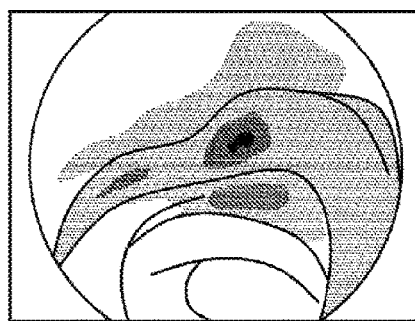
FIG. 6 is display screens of monitors. (a) of FIG. 6 is a display screen of a monitor in a case where a verification mode is not executed, and (b) of FIG. 6 is a display screen of the monitor in a case where the verification mode is executed.
Figure 6:
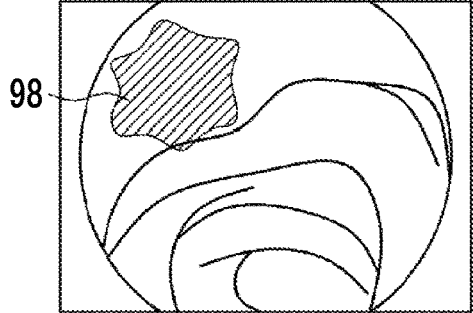
Figure 6:
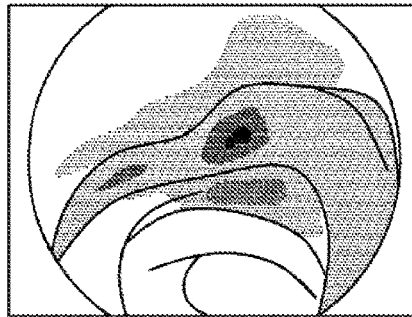

Therefore, in the endoscope system 10, as shown in (b) of FIG. 6, in a case where the verification mode is executed during the oxygen saturation observation mode, the display control unit 48 acquires the correction image 86 that is stored in the storage unit 92 so as to be associated with the oxygen saturation image 96 being displayed, and displays the correction image 86 on the monitor 18 side by side with the oxygen saturation image 96. The verification mode is a mode that makes it possible to verify whether or not pre-imaging has been performed under appropriate conditions in the oxygen saturation observation mode.

In a case where pre-imaging has not been performed under appropriate conditions, there may be a case where the correction image 86 includes, for example, a region that is too bright (hereinafter, referred to as a high brightness region) 98 since the reflection of illumination light is strong (refer to (b) of FIG. 6). In this case, it is difficult to correctly calculate the oxygen saturation correction amount and correct the oxygen saturation. Therefore, by displaying the correction image 86 on the monitor 18 side by side with the oxygen saturation image 96, the doctor can determine whether or not the pre-imaging has been performed under appropriate conditions or whether or not the oxygen saturation image 96 is reliable, and can perform diagnosis based on the oxygen saturation image that accurately shows the oxygen saturation of the observation target. The verification mode may be executed, for example, by operating a selector switch (not shown) provided in the operation unit 12b of the endoscope 12 or by performing an input operation on the console 19 or the like.

Figure 7:
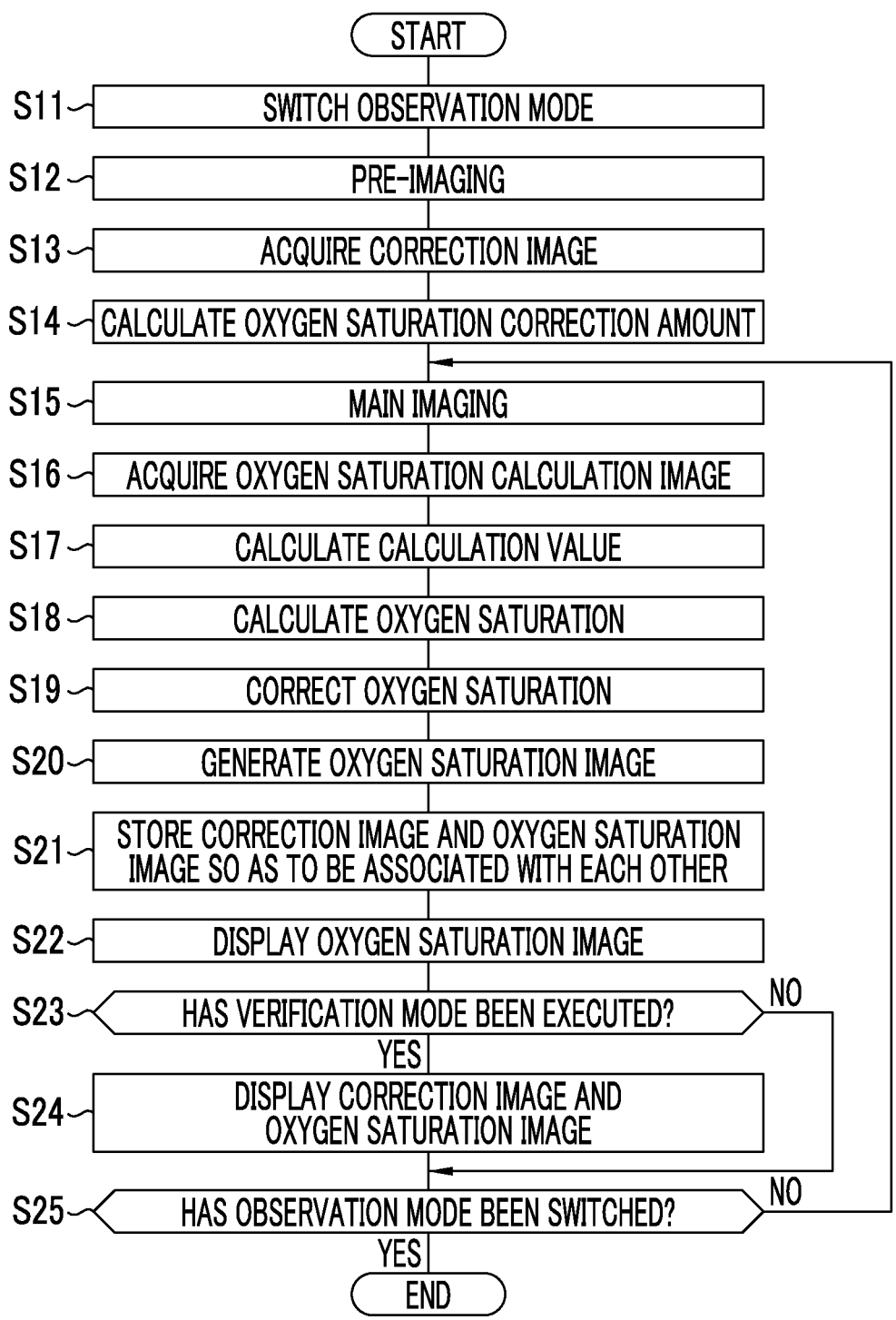
FIG. 7 is a flowchart showing the flow of the operation in an oxygen saturation observation mode.

Next, the flow of the operation of the endoscope system 10 in the case of observing the observation target with the oxygen saturation image will be described with reference to the flowchart shown in FIG. 7. First, the observation mode is switched to the oxygen saturation observation mode using the mode selector switch 13a (S11). By operating the angle knob 12e or the like so that the distal end portion 12d of the endoscope 12 is directed toward a normal part of the observation target, pre-imaging is performed (S12). As a result, the image acquisition unit 44 acquires the correction image 86 (S13).

The oxygen saturation correction amount calculation unit 82 acquires the correction image 86 from the image acquisition unit 44, and calculates the oxygen saturation correction amount 88 with respect to the oxygen saturation calculated by the oxygen saturation calculation unit 73 using the correction image 86 (S14). Specifically, the oxygen saturation correction amount calculation unit 82 calculates representative values of the ratio B1/G and the ratio R/G using the correction image 86, and calculates an oxygen saturation corresponding to the representative values of the ratio B1/G and the ratio R/G with reference to the LUT 75. Then, the oxygen saturation correction amount calculation unit 82 calculates the oxygen saturation correction amount 88 from the relationship between the oxygen saturation as a reference and the actual oxygen saturation calculated using the correction image 86.

Then, the control unit 42 controls each unit to perform the main imaging (S15). The image acquisition unit 44 acquires the oxygen saturation calculation image 76 (S16), and the calculation value calculation unit 71 calculates the ratio B1/G and the ratio R/G using the oxygen saturation calculation image 76 (S17). The oxygen saturation calculation unit 73 calculates the oxygen saturation of the observation target using the ratio B1/G and the ratio R/G and the LUT 75 (S18). The oxygen saturation correction unit 84 corrects the oxygen saturation calculated by the oxygen saturation calculation unit 73 according to the oxygen saturation correction amount 88 calculated by the oxygen saturation correction amount calculation unit 82 (S19).

The oxygen saturation image generation unit 74 generates a base image using the oxygen saturation calculation image 76, and generates the oxygen saturation image 96 by coloring the generated base image using the oxygen saturation (S20). The storage unit 92 stores the oxygen saturation image 96 generated by the oxygen saturation image generation unit 74 and the correction image 86, which has been used for the calculation of the oxygen saturation correction amount and the correction of the oxygen saturation, so as to be associated with each other (S21). The display control unit 48 displays the oxygen saturation image 96 on the monitor 18 (S22). In a case where the verification mode is executed (YES in S23), the display control unit 48 displays the correction image 86 and the oxygen saturation image 96 stored in the storage unit 92 on the monitor 18 side by side (S24). On the other hand, in a case where the verification mode is not executed (NO in S23), the display control unit 48 keeps displaying the oxygen saturation image 96. The generation and display of the oxygen saturation image are repeated until the observation mode is switched to the normal observation mode by using the mode selector switch 13a (S25).

As described above, in the endoscope system 10, the correction image 86 used for the calculation of the oxygen saturation correction amount and the correction of the oxygen saturation is stored in the storage unit 92 so as to be associated with the oxygen saturation image 96, and the correction image 86 and the oxygen saturation image 96 that are stored are displayed side by side in the verification mode. Therefore, the doctor can verify afterward whether or not pre-imaging has been performed under appropriate conditions.

In the first embodiment described above, the storage unit 92 stores the oxygen saturation image 96 and the correction image 86 so as to be associated with each other. However, the storage unit 92 may store not only the oxygen saturation image 96 but also any image, information, and the like so as to be associated with the correction image 86.

Figure 8:
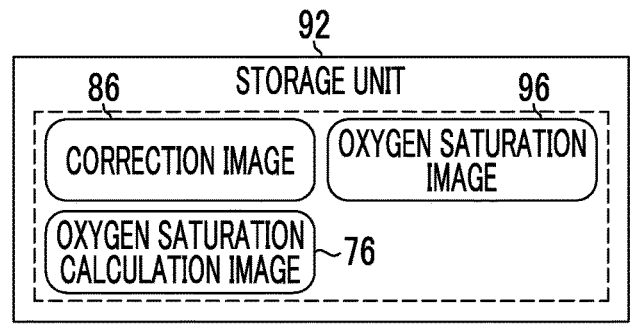
FIG. 8 is a block diagram of a storage unit that stores an oxygen saturation image and an oxygen saturation calculation image so as to be associated with a correction image.

For example, as shown in FIG. 8, the storage unit 92 may store not only the oxygen saturation image 96 but also the oxygen saturation calculation image 76, which is used for generation of the oxygen saturation image 96, so as to be associated with the correction image 86. That is, the B1 image, the B2 image, the G image, and the R image obtained by the main imaging may be stored so as to be associated with the correction image 86. The oxygen saturation calculation image 76 stored in the storage unit 92 is displayed on the monitor 18 side by side with the correction image 86 and the oxygen saturation image 96 in the verification mode. Therefore, the oxygen saturation calculation image 76 stored in the storage unit 92 can be used in a case where the doctor determines whether or not the oxygen saturation image 96 is reliable.

Figure 9:
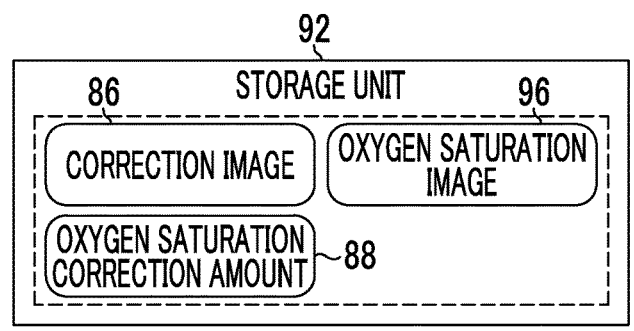
FIG. 9 is a block diagram of a storage unit that stores an oxygen saturation image and an oxygen saturation correction amount so as to be associated with a correction image.

As shown in FIG. 9, the storage unit 92 may store not only the oxygen saturation image 96 but also the oxygen saturation correction amount 88 calculated by the oxygen saturation correction amount calculation unit 82 so as to be associated with the correction image 86. The oxygen saturation correction amount 88 stored in the storage unit 92 is displayed on the monitor 18 side by side with the correction image 86 and the oxygen saturation image 96 in the verification mode. Therefore, the oxygen saturation correction amount 88 stored in the storage unit 92 can be used in a case where the doctor determines whether or not the oxygen saturation image 96 is reliable.

Figure 10:
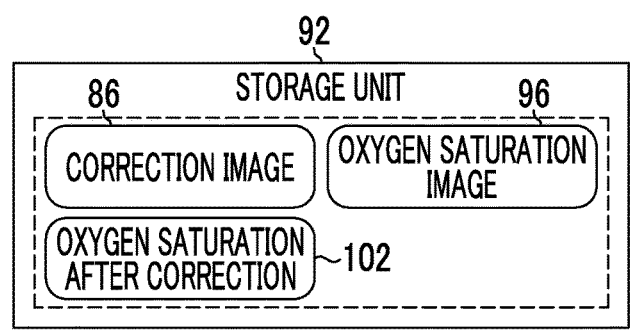
FIG. 10 is a block diagram of a storage unit that stores an oxygen saturation image and an oxygen saturation after correction so as to be associated with a correction image.

As shown in FIG. 10, the storage unit 92 may store not only the oxygen saturation image 96 but also an oxygen saturation 102 after correction by the oxygen saturation correction unit 84 so as to be associated with the correction image 86. The value of the oxygen saturation 102 after correction stored in the storage unit 92 is displayed on the monitor 18 side by side with the correction image 86 and the oxygen saturation image 96 in the verification mode. Therefore, the value of the oxygen saturation 102 after correction stored in the storage unit 92 can be used in a case where the doctor determines whether or not the oxygen saturation image 96 is reliable.

Figure 11:
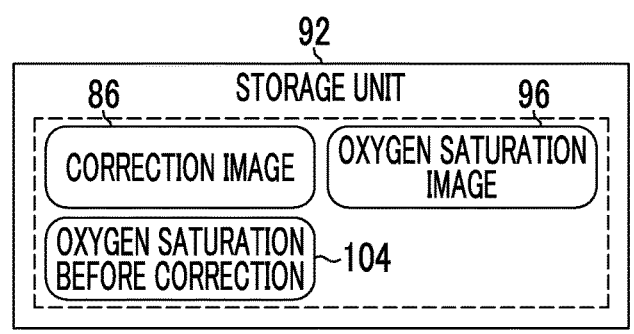
FIG. 11 is a block diagram of a storage unit that stores an oxygen saturation image and an oxygen saturation before correction so as to be associated with a correction image.

As shown in FIG. 11, the storage unit 92 may store not only the oxygen saturation image 96 but also an oxygen saturation 104 before correction by the oxygen saturation correction unit 84, which is calculated by the oxygen saturation calculation unit 73, so as to be associated with the correction image 86. The value of the oxygen saturation 104 before correction stored in the storage unit 92 is displayed on the monitor 18 side by side with the correction image 86 and the oxygen saturation image 96 in the verification mode. Therefore, the value of the oxygen saturation 104 before correction stored in the storage unit 92 can be used in a case where the doctor determines whether or not the oxygen saturation image 96 is reliable.

The storage unit 92 may store not only the oxygen saturation calculation image 76, the oxygen saturation correction amount 88, the oxygen saturation 102 after correction, and the oxygen saturation 104 before correction in the examples described above but also the wavelength information, the average pixel value, the exposure amount, the observation distance, the enlargement ratio, the diagnosis (acquisition) date and time, the patient information, and the like of images stored in the storage unit 92 so as to be associated with the correction image 86. The above-described various images, information, and the like are stored in the storage unit 92 and are displayed on the monitor 18 side by side with the oxygen saturation image 96 instead of or in addition to the correction image 86 in the verification mode, so that the doctor can determine whether or not the oxygen saturation image 96 displayed on the monitor 18 is reliable.

Second Embodiment

In the first embodiment described above, the oxygen saturation correction amount is calculated and the oxygen saturation is corrected by using the correction image 86 acquired from the image acquisition unit 44. However, the calculation of the oxygen saturation correction amount and the correction of the oxygen saturation may be performed again using the correction image 86 stored in the storage unit 92.

Figure 12:
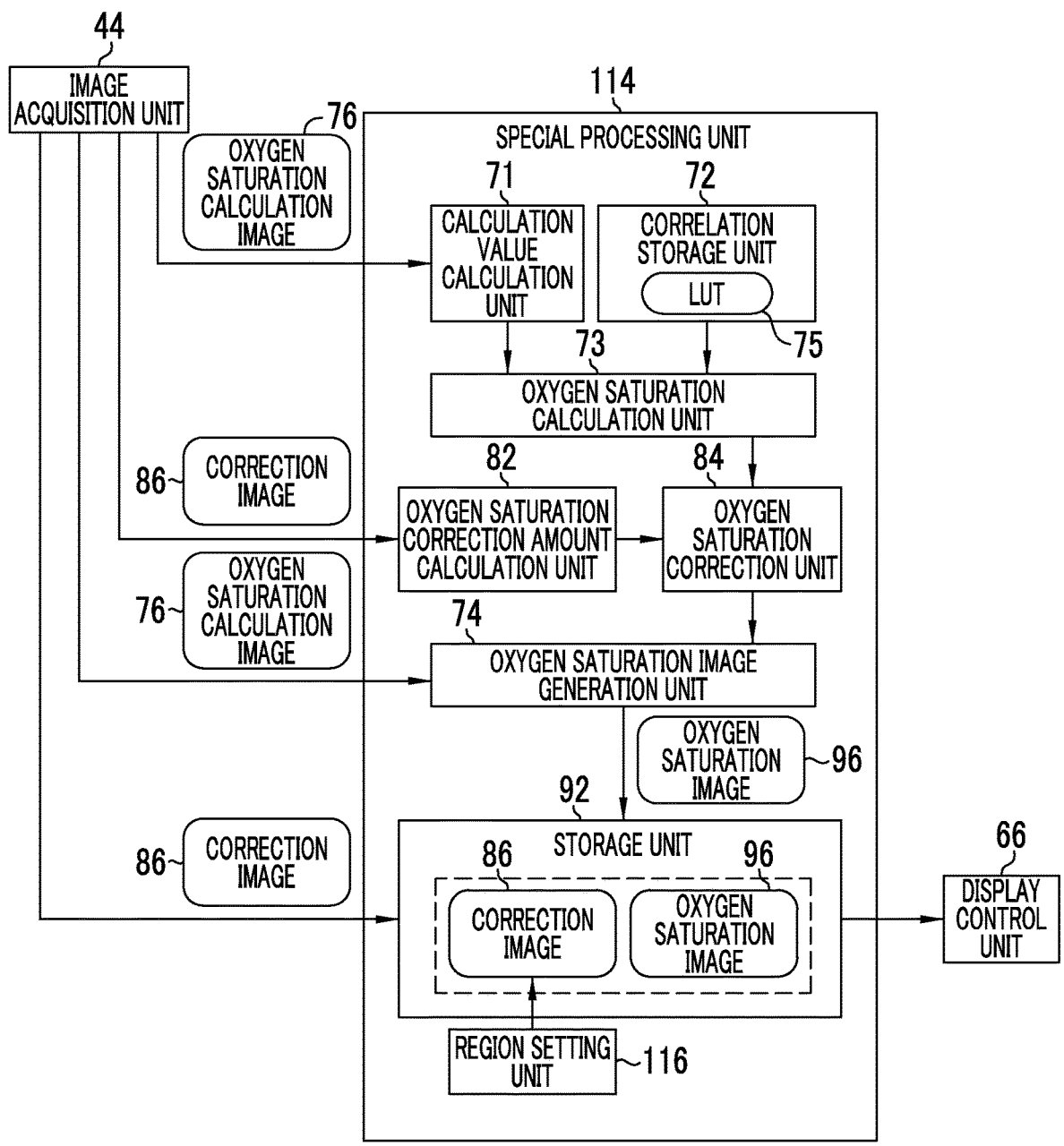
FIG. 12 is a block diagram of a special processing unit having a region setting unit.

In this case, for example, as shown in FIG. 12, the special processing unit 114 has a region setting unit 116 in addition to each unit of the special processing unit 64 of the first embodiment. Since other members are the same as those of the special processing unit 64 of the first embodiment, the explanation thereof will be omitted.

The region setting unit 116 sets a usable region for the correction image 86 stored in the storage unit 92. The usable region is a region satisfying appropriate imaging conditions in a normal part of the observation target. The appropriate imaging conditions include, for example, "not too dark or too bright", "no blur due to relative movement between the observation target and the endoscope", "observation distance is not too short or too long" and "there is no attached matter, such as residues, on the observation target".

Figure 13:
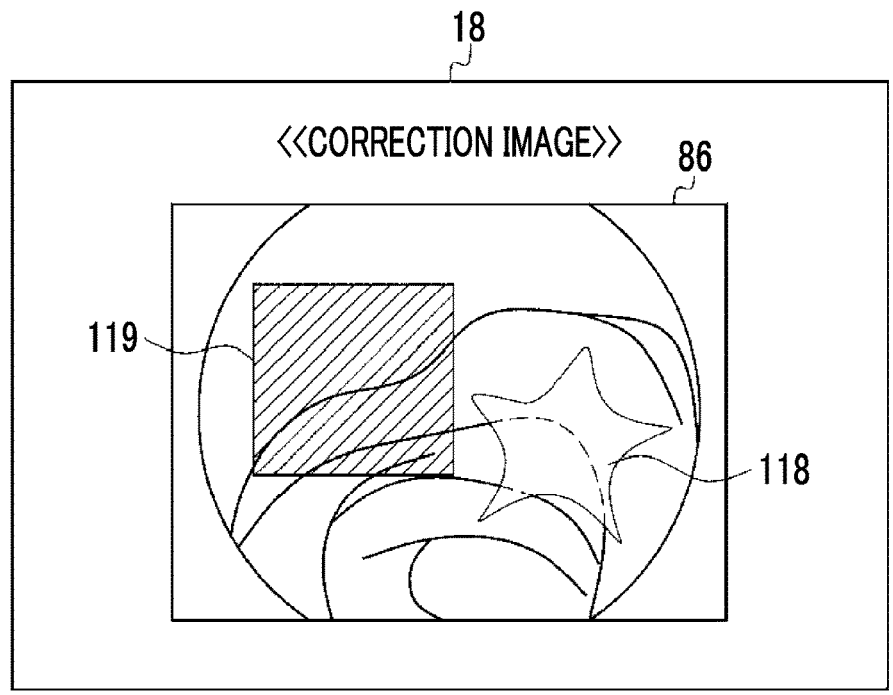
FIG. 13 is an explanatory diagram illustrating a method of designating a usable region.

Even in a case where the user thinks that the normal part of the observation target has been appropriately imaged, for example, as shown in FIG. 13, there may be a case where a high brightness region 118 is generated in the correction image 86 at the moment of imaging. In the high brightness region 118, the values of the ratio B1/G and the ratio R/G are different from those in the case of imaging the normal part of the observation target. Therefore, in a case where the correction image 86 includes the high brightness region 118, it is difficult to correctly calculate the oxygen saturation correction amount and correct the oxygen saturation. The region setting unit 116 sets a usable region 119 so that the high brightness region 118 in the correction image 86 is not included. In addition, the region setting unit 116 may set the usable region 119 based on an input operation on the console 19 or the like.

In a case where the usable region 119 is set by the region setting unit 116, the oxygen saturation correction amount calculation unit 82 re-calculates the oxygen saturation correction amount 88 using the usable region 119. Specifically, the oxygen saturation correction amount calculation unit 82 calculates the oxygen saturation in the usable region 119 by calculating the ratio B1/G and the ratio R/G for the pixels in the usable region 119 using the correction image 86 stored in the storage unit 92. Then, the oxygen saturation correction amount calculation unit 82 re-calculates the oxygen saturation correction amount 88 from the relationship between the calculated oxygen saturation of the usable region 119 and the oxygen saturation as a reference.

The oxygen saturation correction unit 84 corrects the oxygen saturation calculated by the oxygen saturation calculation unit 73 in the same manner as described above by using the oxygen saturation correction amount 88 re-calculated by the oxygen saturation correction amount calculation unit 82. In this manner, by re-calculating the oxygen saturation correction amount and re-correcting the oxygen saturation afterward, it is possible to newly generate an oxygen saturation image that accurately shows the oxygen saturation of the observation target. In addition, the re-calculation of the oxygen saturation correction amount and the re-correction of the oxygen saturation can be performed either during the diagnosis or after the diagnosis.

In addition to designating a region other than the high brightness region 118 as described above, the region setting unit 116 may set the usable region 119 by designating, for example, a region other than a low brightness region that is too dark, a region other than a region where blurring due to movement is relatively large, a region other than a region where the observation distance is too short or too long, a region other than a region where there is attached matter, such as residues, on the observation target.

Figure 14:
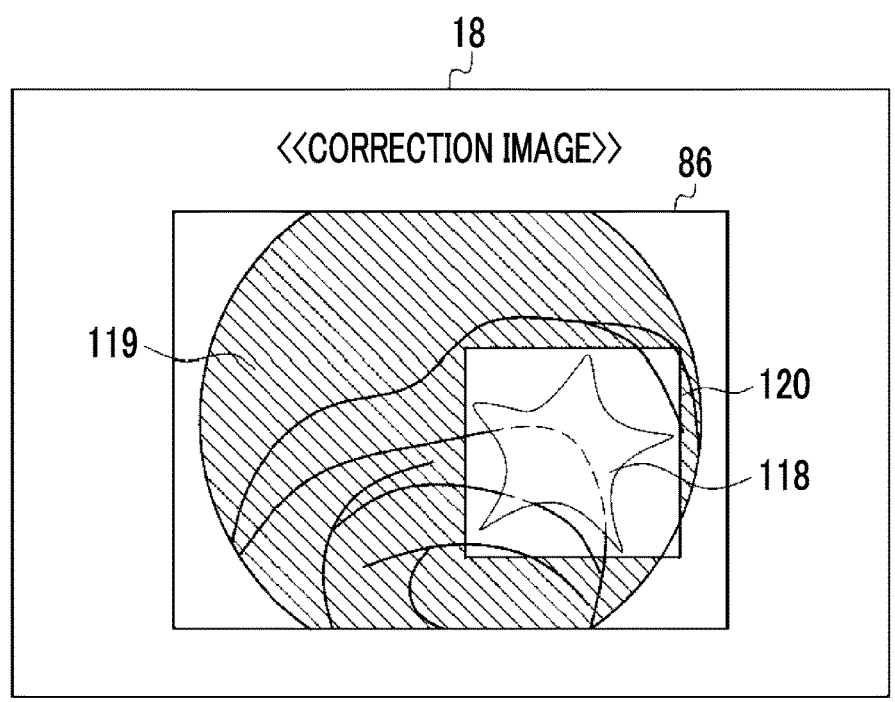
FIG. 14 is an explanatory diagram illustrating a method of designating a region other than an unused region as a usable region.

As shown in FIG. 14, the region setting unit 116 may designate a region including the high brightness region 118 within the correction image 86 as an unused region 120, and set a region other than the unused region 120 as the usable region 119. Also in this case, by re-calculating the oxygen saturation correction amount and re-correcting the oxygen saturation afterward, it is possible to newly generate an oxygen saturation image that accurately shows the oxygen saturation of the observation target.

In the second embodiment described above, the calculation of the oxygen saturation correction amount is performed again using the correction image associated with the oxygen saturation image. However, in preparation for a case where the correction image cannot be acquired under appropriate conditions in pre-imaging, it is preferable to acquire a plurality of sets of correction images by performing pre-imaging multiple times. Each set of correction images is a group of images of four frames of the B1 image, the B2 image, the G image, and the R image obtained by one pre-imaging.

As described above, in a case where pre-imaging is performed multiple times, the storage unit 92 stores a specific set of correction images, among the plurality of sets of correction images, so as to be associated with oxygen saturation images, and stores the other correction images so as not to be associated with the oxygen saturation images.

Then, in the oxygen saturation observation mode, in a case where the doctor executes the verification mode in order to determine whether or not the oxygen saturation image 96 displayed on the monitor 18 is reliable, the oxygen saturation image 96 and the correction image 86 associated with the oxygen saturation image 96 are displayed side by side on the monitor 18 in the same manner as described above. The doctor observes the correction image 86 displayed side by side with the oxygen saturation image 96 to determine whether or not the pre-imaging has been performed under appropriate conditions. The correction image 86 determined that the pre-imaging has not been performed under appropriate conditions is not appropriate as an image used for the calculation of the oxygen saturation correction amount.

In a case where the correction image 86 used for the calculation of the oxygen saturation correction amount is not appropriate, correction images that are not associated with the oxygen saturation image among the correction images stored in the storage unit 92 are displayed on the monitor 18 side by side with the oxygen saturation image by an input operation on the console 19 or the like. For example, the correction images are displayed in order from the correction image whose pre-imaging execution timing is earlier. As a result, the doctor selects a correction image suitable for the calculation of the oxygen saturation correction amount by performing an input operation on the console 19 or the like.

Correction images that are not associated with the oxygen saturation image may be randomly displayed. All the correction images that are not associated with the oxygen saturation image may be listed on the monitor 18, and a correction image selected therefrom may be displayed side by side with the oxygen saturation image. In a case where the appropriate correction image is not stored in the storage unit 92, pre-imaging may be executed again.

The oxygen saturation correction amount calculation unit 82 re-calculates the oxygen saturation correction amount using the selected appropriate correction image. The oxygen saturation correction unit 84 re-corrects the oxygen saturation using the oxygen saturation correction amount re-calculated by the oxygen saturation correction amount calculation unit 82. The re-calculation of the oxygen saturation correction amount and the re-correction of the oxygen saturation described above can be performed either during the diagnosis or after the diagnosis.

As described above, by changing the set of correction images to be used in a case where the oxygen saturation correction amount calculation unit 82 calculates the oxygen saturation correction amount and re-calculating the oxygen saturation correction amount and re-correcting the oxygen saturation, it is possible to newly generate an oxygen saturation image that accurately shows the oxygen saturation of the observation target.

The image acquisition unit 44 may acquire the correction image again by executing the pre-imaging again during the diagnosis. Specifically, in a case where the image used for the calculation of the oxygen saturation correction amount by the oxygen saturation correction amount calculation unit 82 is the inappropriate correction image 86, the image acquisition unit 44 re-acquires the correction image. Whether or not the correction image 86 is inappropriate can be determined, for example, by the doctor whose executes the verification mode during the oxygen saturation observation mode and observing the oxygen saturation image 96 and the correction image 86 displayed side by side on the monitor 18. Re-acquisition of the correction image is executed by, for example, an operation of inputting a pre-imaging instruction using the console 19 or the like.

Then, the oxygen saturation correction amount calculation unit 82 re-calculates the oxygen saturation correction amount using the re-acquired new correction image. The oxygen saturation correction unit 84 re-corrects the oxygen saturation using the oxygen saturation correction amount re-calculated by the oxygen saturation correction amount calculation unit 82. As a result, during the diagnosis, an oxygen saturation image that accurately shows the oxygen saturation of the observation target can be newly generated.

The storage unit 92 may store the new correction image re-acquired by the image acquisition unit 44 so as to be associated with the oxygen saturation image.

The oxygen saturation image is used not only for observing the observation target in real time during the diagnosis but also for checking the diagnosis result again after completing the diagnosis and for observing the state of the observed part and its surroundings in more detail. During diagnosis, it is required to display a motion picture of oxygen saturation images in real time, but after the diagnosis, it is required to display an oxygen saturation image that accurately shows the oxygen saturation of the observation target.

For this reason, between a case where the image acquisition unit 44 acquires the oxygen saturation calculation image 76 and the correction image 86 in real time during the diagnosis and a case where the image acquisition unit 44 acquires the oxygen saturation calculation image 76 and the correction image 86 after the diagnosis, the accuracy of the calculation of the oxygen saturation correction amount and the correction of the oxygen saturation may be changed. In the present embodiment, the accuracy of the calculation of the oxygen saturation correction amount and the correction of the oxygen saturation is changed by changing the number of pixels for executing the calculation of the oxygen saturation correction amount and the correction of the oxygen saturation between the case where the oxygen saturation calculation image 76 and the correction image 86 are acquired during the diagnosis and the case where the oxygen saturation calculation image 76 and the correction image 86 are acquired after the diagnosis.

Specifically, in a case where each image is acquired after the diagnosis, the calculation of the oxygen saturation correction amount and the correction of the oxygen saturation degree are executed for all the pixels. On the other hand, in a case where each image is acquired during the diagnosis, the calculation of the oxygen saturation correction amount and the correction of the oxygen saturation degree are executed for some of all the pixels (for example, ½ pixels or ⅔ pixels of all the pixels). Therefore, the accuracy of the calculation of the oxygen saturation correction amount and the accuracy of the correction of the oxygen saturation in the case where each image is acquired after the diagnosis is higher than the accuracy of the calculation of the oxygen saturation correction amount and the accuracy of the correction of the oxygen saturation in the case where each image is acquired in real time during the diagnosis.

Figure 15:
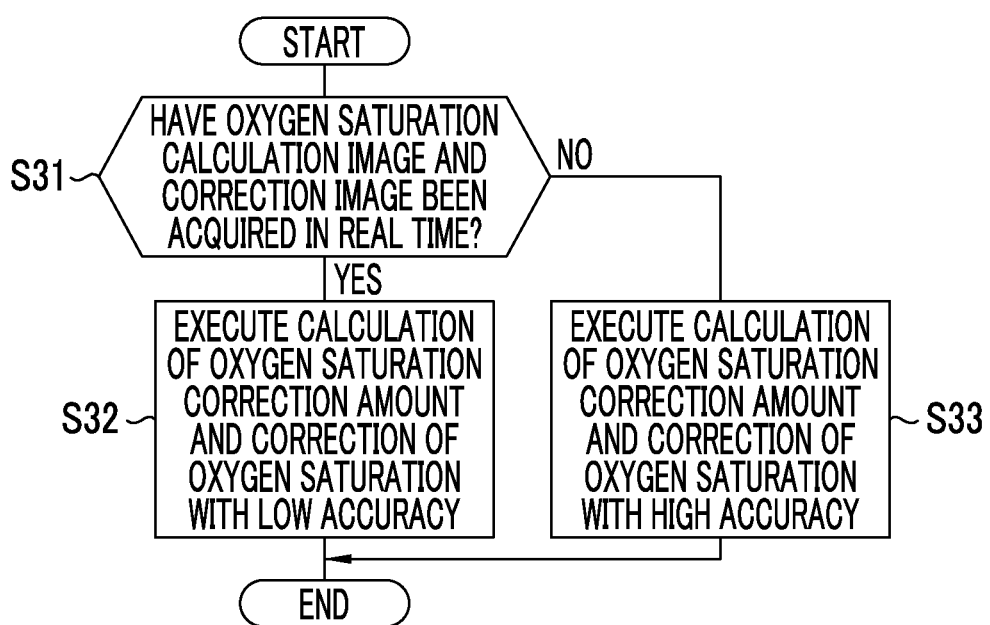
FIG. 15 is a flowchart illustrating changes in the calculation accuracy of the oxygen saturation correction amount and the correction accuracy of the oxygen saturation.

As shown in FIG. 15, in a case where the image acquisition unit 44 acquires the oxygen saturation calculation image 76 and the correction image 86 in real time (YES in S31), the calculation of the oxygen saturation correction amount is performed with low accuracy by the oxygen saturation correction amount calculation unit 82, and the correction of the oxygen saturation is performed with low accuracy by the oxygen saturation correction unit 84 (S32). On the other hand, in a case where the image acquisition unit 44 does not acquire the oxygen saturation calculation image 76 and the correction image 86 in real time (NO in S31), the calculation of the oxygen saturation correction amount is performed with high accuracy by the oxygen saturation correction amount calculation unit 82, and the correction of the oxygen saturation is performed with high accuracy by the oxygen saturation correction unit 84 (S33).

As a result, after the diagnosis, an oxygen saturation image that accurately shows the oxygen saturation of the observation target can be displayed. In addition, during the diagnosis, it is possible to suppress the degradation of the image quality of the motion picture due to lowering in real-time performance. As a result, the motion picture of oxygen saturation images can be displayed with high image quality.

Third Embodiment

In the first and second embodiments described above, the oxygen saturation image 96 showing the oxygen saturation after correction is stored in the storage unit 92 so as to be associated with the correction image 86. In the third embodiment, the oxygen saturation calculation image 76 as a biometric feature amount calculation image is corrected based on the correction image 86, and the oxygen saturation is calculated using the corrected oxygen saturation calculation image 76, thereby generating an oxygen saturation image 130 (refer to FIG. 16) as a first biometric feature amount image. Therefore, the oxygen saturation image 130 is stored in the storage unit 92 so as to be associated with the correction image 86. In the third embodiment, an example will be described in which pre-imaging is performed before the main imaging as in the first embodiment. However, the pre-imaging may be performed after the main imaging without being limited thereto.

Figure 16:
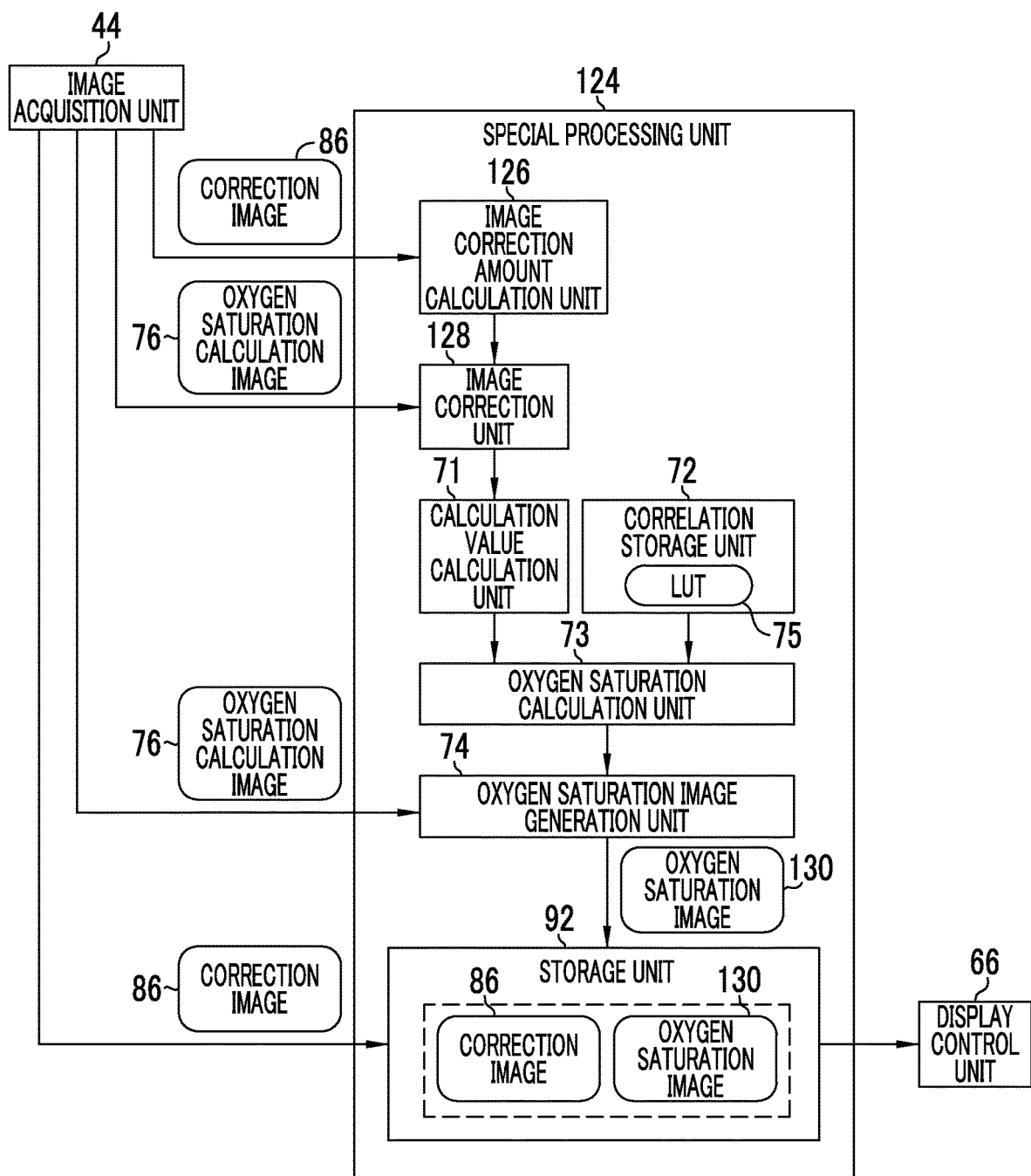
FIG. 16 is a block diagram of a special processing unit of a third embodiment.

As shown in FIG. 16, a special processing unit 124 of the third embodiment has an image correction amount calculation unit 126 and an image correction unit 128 instead of the oxygen saturation correction amount calculation unit 82 and the oxygen saturation correction unit 84 provided in the special processing unit 64 of the first embodiment.

The image correction amount calculation unit 126 acquires the correction image 86 from the image acquisition unit 44, and calculates an image correction amount for correcting the oxygen saturation calculation image 76 using the acquired correction image 86. Specifically, the image correction amount calculation unit 126 calculates the image correction amount using the pixel values of the B1 image, the G image, and the R image of the correction image 86 obtained by pre-imaging.

In the third embodiment, pre-imaging is performed for correction of the oxygen saturation calculation image 76. In the pre-imaging, a normal part of the observation target is imaged. Therefore, in a case where the observation target is an ideal observation target, the pixel values of the B1 image, the G image, and the R image are specific values. For example, for the B1 image, the G image, and the R image obtained by imaging a normal part of an ideal observation target, the pixel values of a certain pixel are a pixel value $B1^a$, a pixel value $G^a$, and a pixel value $R^a$. On the other hand, there are individual differences in actual observation targets, and the pixel values of the B1 image, the G image, and the R image obtained by imaging the actual observation target are, for example, a pixel value $B1^b$, a pixel value $G^b$, and a pixel value $R^b$.

In this case, the image correction amount calculation unit 126 calculates an image correction amount ΔB1 from the pixel value $B1^a$ in the case of imaging the normal part and the pixel value $B1^b$ in the case of imaging the actual observation target. Similarly, the image correction amount calculation unit 126 calculates an image correction amount ΔG from the pixel value $G^a$ and the pixel value $G^b$, and calculates an image correction amount ΔR from the pixel value $R^a$ and the pixel value $R^b$. For example, the image correction amount calculation unit 126 sets a value, which is obtained by subtracting the pixel value $B1^b$ from the pixel value $B1^a$, as the image correction amount ΔB1. Similarly, the image correction amount calculation unit 126 sets a value, which is obtained by subtracting the pixel value $G^b$ from the pixel value $G^a$, as the image correction amount ΔG, and sets a value, which is obtained by subtracting the pixel value $R^b$ from the pixel value $R^a$, as the image correction amount ΔR. The image correction amount calculation unit 126 calculates the image correction amount each time the correction image 86 is acquired.

The image correction unit 128 corrects the oxygen saturation calculation image 76 acquired from the image acquisition unit 44 using the image correction amount calculated by the image correction amount calculation unit 126. Specifically, the image correction unit 128 corrects the pixel value B1, the pixel value G, and the pixel value R of the B1 image, the G image, and the R image of the oxygen saturation calculation image 76 using the image correction amounts ΔB1, ΔG, and ΔR.

For example, in a case where the pixel values of a certain pixel of the B1 image, the G image, and the R image of the oxygen saturation calculation image 76 are a pixel value B1*, a pixel value G*, and a pixel value R*, respectively, the image correction unit 128 calculates a corrected pixel value $B1^\#$ by adding the image correction amount ΔB1 to the pixel value B1*, calculates a corrected pixel value $G^\#$ by adding the image correction amount ΔG to the pixel value G*, and calculates a corrected pixel value $R^\#$ by adding the image correction amount ΔR to the pixel value R*. A $B1^\#$ image having the corrected pixel value $B1^\#$, a $G^\#$ image having the corrected pixel value $G^\#$, and an $R^\#$ image having the corrected pixel value $R^\#$ are referred to as corrected oxygen saturation calculation images. The image correction unit 128 corrects the oxygen saturation calculation image 76 each time the oxygen saturation calculation image 76 is acquired. In the case of adding the image correction amount to the pixel value of the oxygen saturation calculation image 76, the image correction unit 128 may multiply the pixel value of the oxygen saturation calculation image 76 by a specific coefficient. The image correction unit 128 outputs the corrected oxygen saturation calculation image to the calculation value calculation unit 71.

Figure 17:
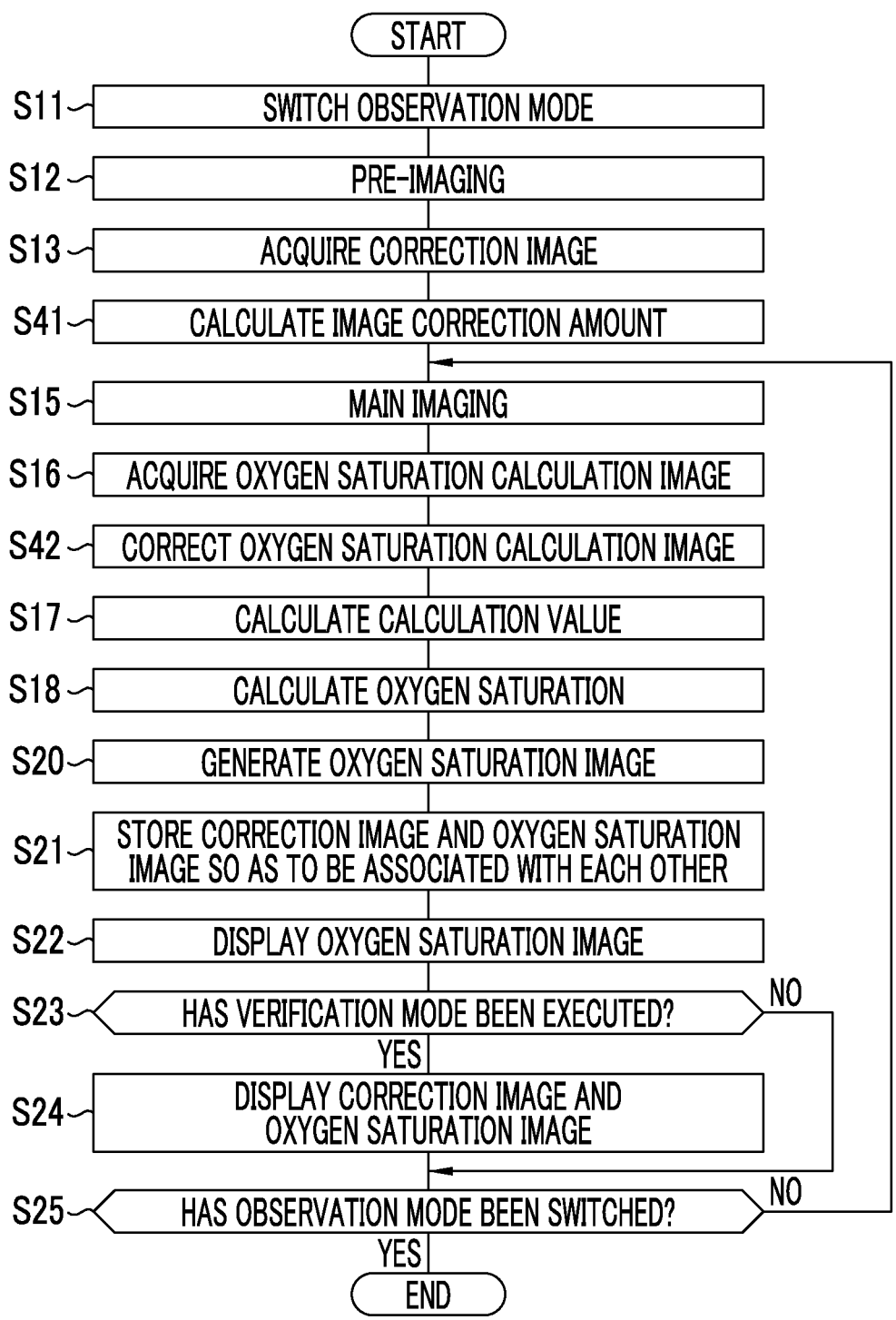
FIG. 17 is a flowchart showing the flow of the operation in the oxygen saturation observation mode of a third embodiment.

Next, the flow of the operation in the oxygen saturation observation mode of the third embodiment will be described with reference to a flowchart shown in FIG. 17. First, as in the first embodiment, the observation mode is switched to the oxygen saturation observation mode (S11), and pre-imaging is performed (S12). As a result, the image acquisition unit 44 acquires the correction image 86 (S13).

The image correction amount calculation unit 126 acquires the correction image 86 from the image acquisition unit 44, and calculates an image correction amount, which is for correcting the oxygen saturation calculation image 76 obtained by the main imaging, using the correction image 86 (S41). Then, the control unit 42 controls each unit to perform the main imaging (S15), and the image acquisition unit 44 acquires the oxygen saturation calculation image 76 (S16).

The image correction unit 128 corrects the oxygen saturation calculation image 76 acquired from the image acquisition unit 44 using the image correction amount calculated by the image correction amount calculation unit 126 (S42).

The calculation value calculation unit 71 performs a calculation using the pixel value of the corrected oxygen saturation calculation image, thereby calculating a calculation value used for the calculation of the oxygen saturation (S17). Specifically, the calculation value calculation unit 71 calculates a ratio $B1^\#/G^\#$ between the $B1^\#$ image and the $G^\#$ image and a ratio $R^\#/G^\#$ between the $R^\#$ image and the $G^\#$ image for each pixel.

The oxygen saturation calculation unit 73 as a biometric feature amount calculation unit calculates an oxygen saturation corresponding to the ratios $B1^\#/G^\#$ and $R^\#/G^\#$ calculated by the calculation value calculation unit 71 with reference to the LUT 75 stored in the correlation storage unit 72 (S18). As a result, the influence of individual differences in observation targets and the like on the oxygen saturation calculated by the oxygen saturation calculation unit 73 is reduced.

The oxygen saturation image generation unit 74 generates the oxygen saturation image 130, which shows the oxygen saturation calculated by the oxygen saturation calculation unit 73, using the corrected oxygen saturation calculation image (S20).

The storage unit 92 stores the correction image 86 and the oxygen saturation image 130 so as to be associated with each other (S21). Since subsequent steps are the same as steps S22 to S25 in the first embodiment, the explanation thereof will be omitted. Thus, as in each of the embodiments described above, by displaying the stored correction image 86 and oxygen saturation image 130 side by side on the monitor 18 as a display unit in the verification mode, it is possible to verify afterward whether or not pre-imaging has been performed under appropriate conditions.

In the third embodiment described above, the image correction unit 128 corrects the B1 image, the G image, and the R image of the oxygen saturation calculation image 76. However, the image correction unit 128 may correct the ratio B1/G and the ratio R/G calculated by the calculation value calculation unit 71.

In this case, the image correction amount calculation unit 126 calculates an image correction amount ΔD1 from the ratio $B1^a/G^a$ in the case of imaging the normal part of the ideal observation target and the ratio $B1^b/G^b$ in the case of imaging the actual observation target, and an image correction amount ΔD2 from the ratio $R^a/G^a$ in the case of imaging the normal part of the ideal observation target and the ratio $R^b/G^b$ in the case of imaging the actual observation target. For example, in the same manner as described above, the image correction amount calculation unit 126 sets the difference between the ratio $B1^a/G^a$ and the ratio $B1^b/G^b$ as the image correction amount $\Delta D1$, and sets the difference between the ratio $R^a/G^a$ and the ratio $R^b/G^b$ as the image correction amount $\Delta D2$.

Then, the image correction unit 128 corrects the ratio $B1*/G*$ with the image correction amount $\Delta D1$ to calculate the ratio $B1^\#/G^\#$, and corrects the ratio $R*/G*$ with the image correction amount $\Delta D2$ to calculate the ratio $R^\#/G^\#$. The image correction unit 128 outputs the calculated ratios $B1^\#/G^\#$ and $R*/G*$ to the oxygen saturation calculation unit 73.

The oxygen saturation calculation unit 73 calculates an oxygen saturation corresponding to the ratios $B1^\#/G^\#$ and $R*/G*$ with reference to the LUT 75 stored in the correlation storage unit 72. As a result, as described above, the influence of individual differences in observation targets and the like on the oxygen saturation calculated by the oxygen saturation calculation unit 73 is reduced.

In the third embodiment described above, the oxygen saturation image 130 is stored in the storage unit 92 so as to be associated with the correction image 86. However, in addition to the oxygen saturation image 130, the oxygen saturation or the like calculated by the oxygen saturation calculation unit 73 using the corrected oxygen saturation calculation image, the oxygen saturation calculation image before correction, the image correction amount, and the corrected oxygen saturation calculation image may be stored in the storage unit 92 so as to be associated with the correction image 86.

In a case where the region setting unit 116 sets a usable region for the correction image 86 stored in the storage unit 92 as in the second embodiment described above, the calculation of the image correction amount and the correction of the oxygen saturation calculation image may be performed again. That is, the image correction amount calculation unit 126 re-calculates the image correction amount in the same manner as described above using the usable region set by the region setting unit 116. The image correction unit 128 re-corrects the oxygen saturation calculation image 76 using the image correction amount re-calculated by the image correction amount calculation unit 126. As in the second embodiment described above, the region setting unit 116 may set a region other than an unused region as a usable region by setting the unused region for the correction image 86.

In preparation for a case where the correction image 86 cannot be acquired under appropriate conditions in pre-imaging, it is preferable to acquire a plurality of sets of correction images 86 by performing pre-imaging multiple times and store the plurality of sets of correction images 86 in the storage unit 92. In this manner, even in a case where the correction image 86 used for the calculation of the image correction amount by the image correction amount calculation unit 126 is not appropriate, the image correction amount calculation unit 126 can change the set of correction images 86 to re-calculate the image correction amount. In a case where the image correction amount is re-calculated, the image correction unit 128 re-corrects the oxygen saturation calculation image 76.

In a case where the correction image 86 cannot be acquired under appropriate conditions in pre-imaging, the pre-imaging may be executed again during the diagnosis so that the image acquisition unit 44 re-acquires the correction image. In this case, the image correction amount calculation unit 126 re-calculates the image correction amount using the new correction image re-acquired by the image acquisition unit 44. As described above, the image correction unit 128 re-corrects the oxygen saturation calculation image 76 using the image correction amount re-calculated by the image correction amount calculation unit 126. The storage unit 92 may store the new correction image re-acquired by the image acquisition unit 44 so as to be associated with the oxygen saturation image 130.

The accuracy of the calculation of the image correction amount by the image correction amount calculation unit 126 and the accuracy of the correction of the oxygen saturation calculation image 76 by the image correction unit 128 may be changed depending on whether or not the image acquisition unit 44 has acquired the oxygen saturation calculation image 76 and the correction image 86 in real time. Specifically, the accuracy of the calculation of the image correction amount and the accuracy of the correction of the oxygen saturation calculation image 76 in a case where the image acquisition unit 44 acquires the oxygen saturation calculation image 76 and the correction image 86 after the diagnosis is higher than the accuracy of the calculation of the image correction amount and the accuracy of the correction of the oxygen saturation calculation image 76 in a case where the image acquisition unit 44 acquires the oxygen saturation calculation image 76 and the correction image 86 in real time.

Fourth Embodiment

Figure 18:
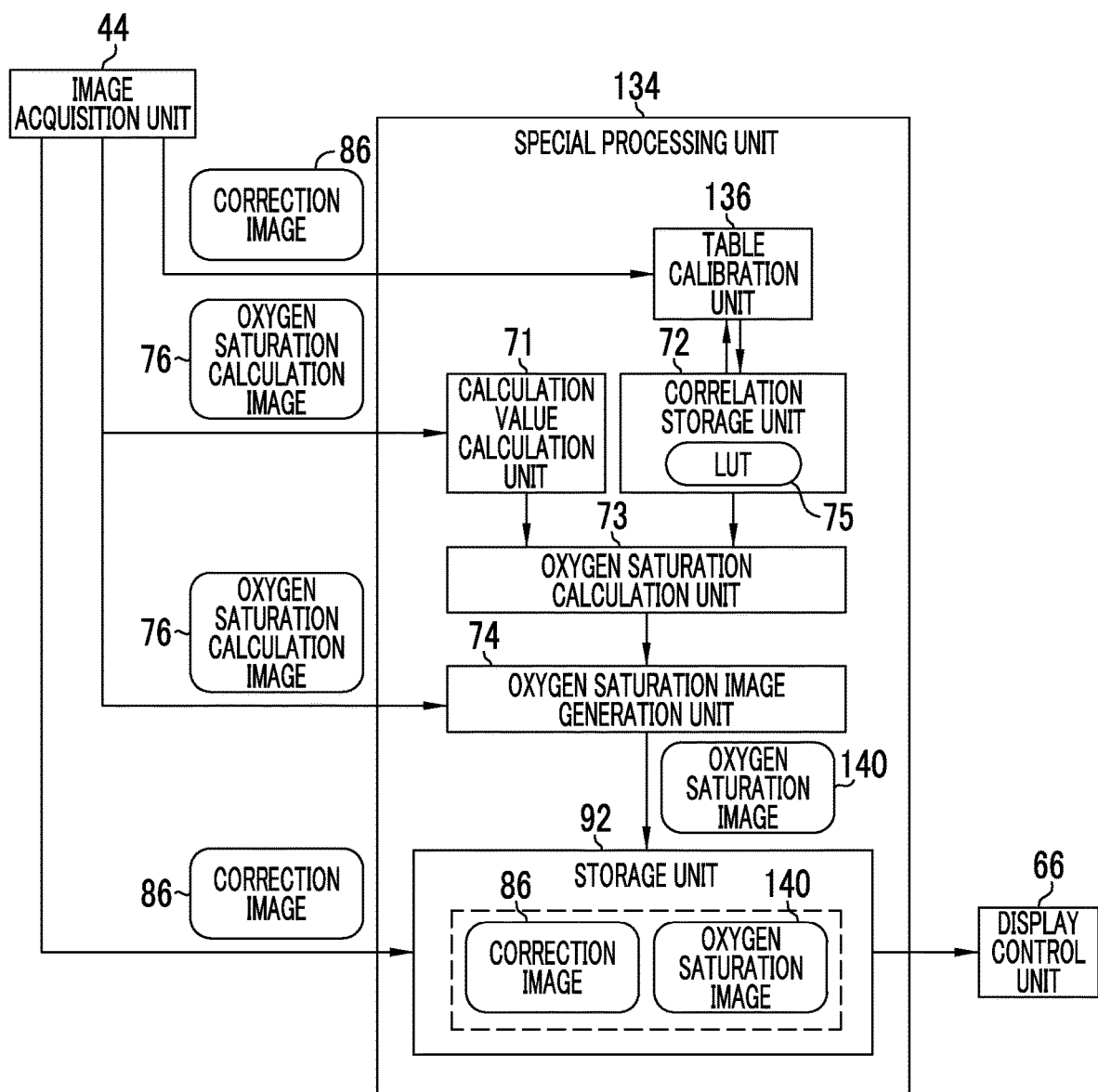
FIG. 18 is a block diagram of a special processing unit of a fourth embodiment.

In the first and second embodiments described above, the oxygen saturation is corrected. However, instead of correcting the oxygen saturation, the LUT 75 may be calibrated. As shown in FIG. 18, a special processing unit 134 of the fourth embodiment has a table calibration unit 136 instead of the oxygen saturation correction amount calculation unit 82 and the oxygen saturation correction unit 84 provided in the special processing unit 64 of the first embodiment. Since other members are the same as those of the special processing unit 64 of the first embodiment, the explanation thereof will be omitted.

The table calibration unit 136 acquires the correction image 86 from the image acquisition unit 44, and calibrates the LUT 75 using the correction image 86. Specifically, the table calibration unit 136 calculates the ratio B1/G and the ratio R/G for each pixel using the B1 image, the G image, and the R image of the correction image 86, and calibrates the LUT 75 using the representative value of the calculated ratio B1/G and the representative value of the calculated ratio R/G. The representative values of the ratio B1/G and the ratio R/G may be average values, median values, mode values, and the like, or other statistics may be used as representative values.

Figure 19:
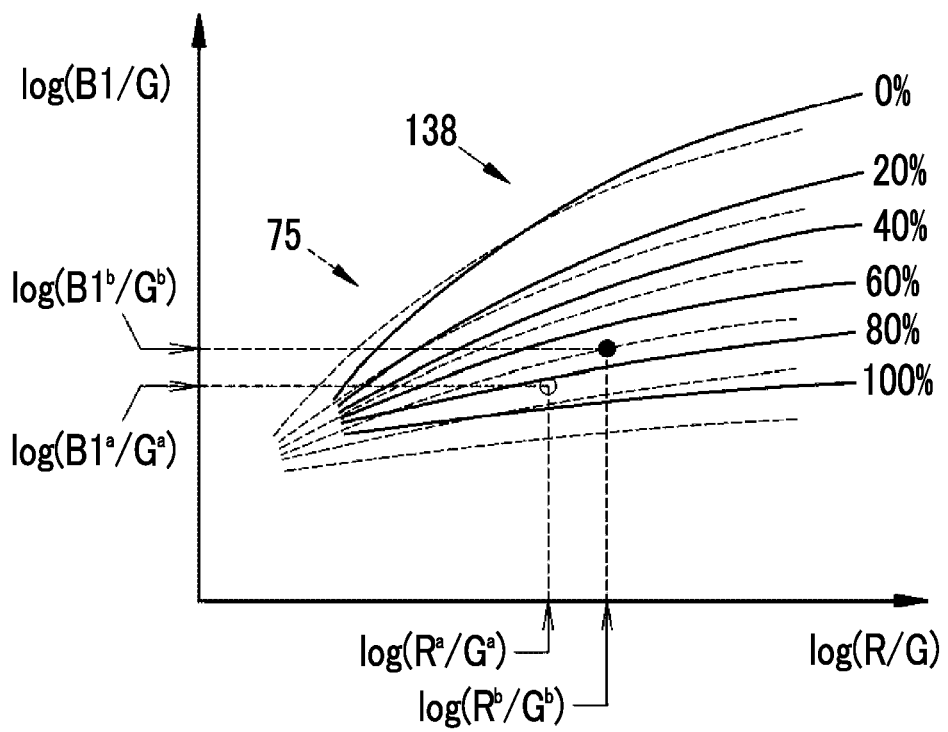
FIG. 19 is a graph showing a method of calibrating an LUT used for the calculation of the oxygen saturation.

In the pre-imaging, a normal part of the observation target is imaged. Therefore, in a case where the observation target is an ideal observation target assumed in the simulation for calculating the LUT 75, the representative value of the ratio B1/G, the representative value of the ratio R/G, and the value of the oxygen saturation associated with the representative values of these ratios by the LUT 75 have specific values. For example, as shown in FIG. 19, the representative value of the ratio B1/G calculated using an image obtained by imaging the normal part of the ideal observation target is $B1^a/G^a$, and the representative value of the ratio R/G is $R^a/G^a$. Therefore, the oxygen saturation is 70%. On the other hand, since there are individual differences in actual observation targets and the like, there is a deviation in the representative values of the ratio B1/G and the ratio R/G calculated by using the correction image 86 obtained by imaging the actual observation target. Therefore, it is assumed that the representative value of the ratio B1/G is $B1^b/G^b$ and the representative value of the ratio R/G is $R^b/G^b$. In this case, in a case where the oxygen saturation is calculated using the LUT 75, the value of the oxygen saturation is 60%.

However, the value of the oxygen saturation is hardly influenced by individual differences in observation targets and the like. Therefore, in a case where a normal part is observed, the value of the oxygen saturation is approximately fixed (for example, 70%) in all observation targets. For this reason, as shown in FIG. 19, the table calibration unit 136 moves the isolines indicated by the LUT 75 to modify the content of the LUT 75 so as to become a value (70%) in the case of observing the normal part from the ratio $B1^b/G^b$ and the ratio $R^b/G^b$ calculated using the correction image 86. This is the calibration performed by the table calibration unit 136.

The relative positional relationship between the isolines of the LUT 75 before calibration with respect to the ratio $B1^a/G^a$ and the ratio $R^a/G^a$ and the relative positional relationship between the isolines of an LUT 138 after calibration with respect to the ratio $B1^b/G^b$ and the ratio $R^b/G^b$ are equal. In a case where the table calibration unit 136 calibrates the LUT 75, the oxygen saturation calculation unit 73 calculates the oxygen saturation in the same manner as described above by using the LUT 138 after calibration. Therefore, the influence of individual differences in observation targets and the like on the oxygen saturation calculated by the oxygen saturation calculation unit 73 is reduced.

The oxygen saturation image generation unit 74 generates an oxygen saturation image 140 as a second biometric feature amount image, which shows the oxygen saturation calculated using the LUT 138 after the calibration by the oxygen saturation calculation unit 73.

The storage unit 92 stores the correction image 86 and the oxygen saturation image 140 so as to be associated with each other. Thus, as in each of the embodiments described above, by displaying the stored correction image 86 and oxygen saturation image 140 side by side in the verification mode, it is possible to verify afterward whether or not pre-imaging has been performed under appropriate conditions.

Fifth Embodiment

In a fifth embodiment, the observation target is illuminated using a laser light source and a phosphor instead of the four LEDs 20a to 20d shown in the first embodiment. Others are the same as in the first embodiment.

Figure 20:
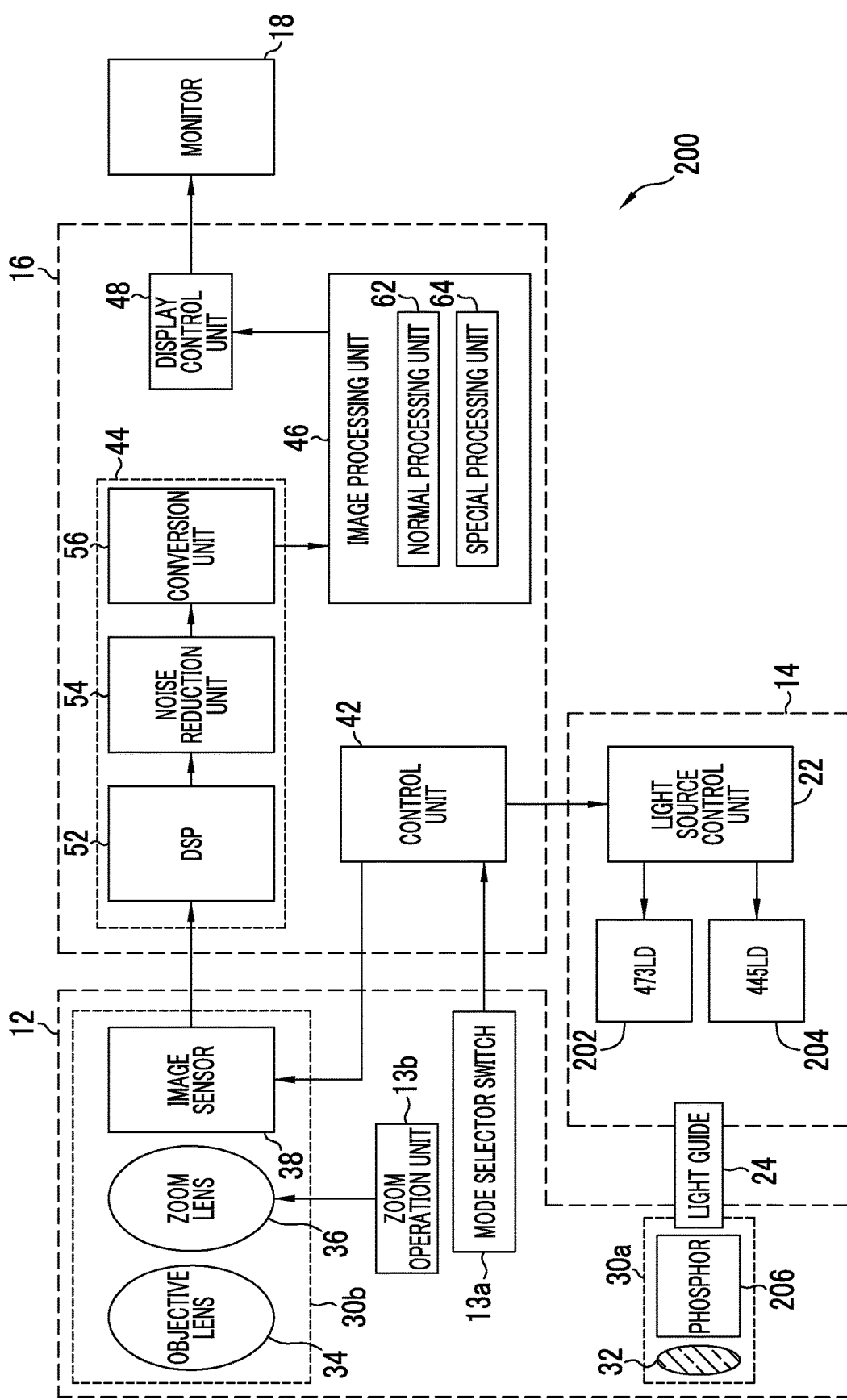
FIG. 20 is a block diagram of an endoscope system of a fifth embodiment.

As shown in FIG. 20, in an endoscope system 200 of the fifth embodiment, instead of the four LEDs 20a to 20d provided in the endoscope system 10 of the first embodiment, a first blue laser light source (denoted as "473LD" in FIG. 20) 202 that emits first blue laser light having a center wavelength of 473 nm and a second blue laser light source (denoted as "445LD" in FIG. 20) 204 that emits second blue laser light having a center wavelength of 445 nm are provided in the light source device 14. The LD is a laser diode. Emission of the first blue laser light source 202 and the second blue laser light source 204 formed of semiconductor light emitting elements is individually controlled by the light source control unit 22. Therefore, the light amount ratio between the light amount of the first blue laser light source 202 and the light amount of the second blue laser light source 204 can be freely changed.

The light source control unit 22 turns on the second blue laser light source 204 in the case of the normal observation mode. On the other hand, in the case of the oxygen saturation observation mode, the first blue laser light source 202 and the second blue laser light source 204 are alternately turned on at intervals of one frame.

It is preferable that the half-width of the first blue laser light or/and the second blue laser light is set to approximately ±10 nm. As the first blue laser light source 202 and the second blue laser light source 204, a broad area type InGaN-based laser diode can be used, or an InGaNAs-based laser diode or a GaNAs-based laser diode can be used. As the light sources, a structure using a light emitter, such as a light emitting diode, may be used.

In addition to the illumination lens 32, a phosphor 206 on which the first blue laser light or the second blue laser light from the light guide 24 is incident is provided in the illumination optical system 30a. The phosphor 206 is excited by the second blue laser light and emits fluorescence. The phosphor 206 is also excited by the first blue laser light. In this case, however, the phosphor 206 emits fluorescence with a smaller amount of light emission than the fluorescence emitted by the second blue laser light. A part of the second blue laser light is transmitted without exciting the phosphor 206. The first blue laser light is almost transmitted without exciting the phosphor 206. The inside of the body of the observation target is illuminated with the light, which is emitted from the phosphor 206, through the illumination lens 32.

As the phosphor 206, it is preferable to use a phosphor configured to include a plurality of kinds of phosphors (for example, a YAG-based phosphor or a phosphor, such as BAM ($BaMgAl_{10}O_{17}$)) that absorb a part of the first blue laser light and the second blue laser light and are excited to emit green to yellow light beams. In a case where the semiconductor light emitting element is used as the excitation light source of the phosphor 206 as in this configuration example, high-intensity white light can be obtained with high luminous efficiency. Therefore, it is possible to easily adjust the intensity of white light and to suppress the change in color temperature and chromaticity of white light.

Figure 21:
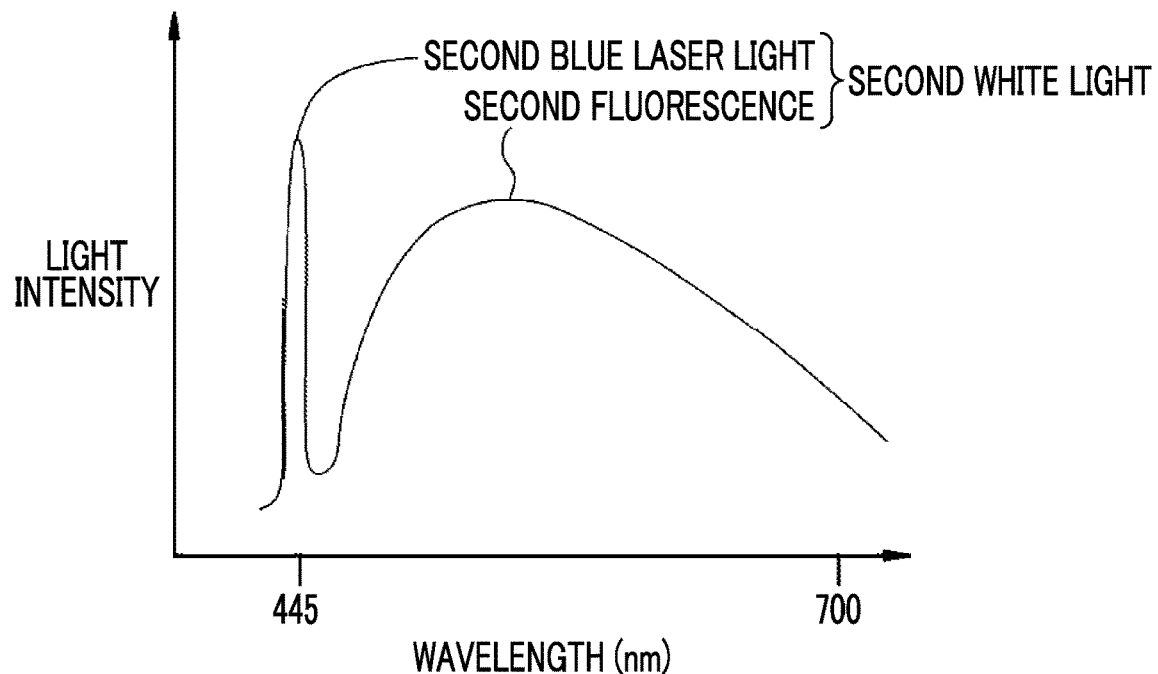
FIG. 21 is a graph showing the spectrum of light emitted in a normal observation mode.

In the normal observation mode, the second blue laser light is incident on the phosphor 206. Accordingly, the observation target is illuminated with white light having a spectrum shown in FIG. 21 (second white light). The second white light is configured to include second blue laser light and second fluorescence of green to red that is excited and emitted from the phosphor 206 by the second blue laser light. Accordingly, the wavelength range of the second white light is the entire visible light region.

Figure 22:
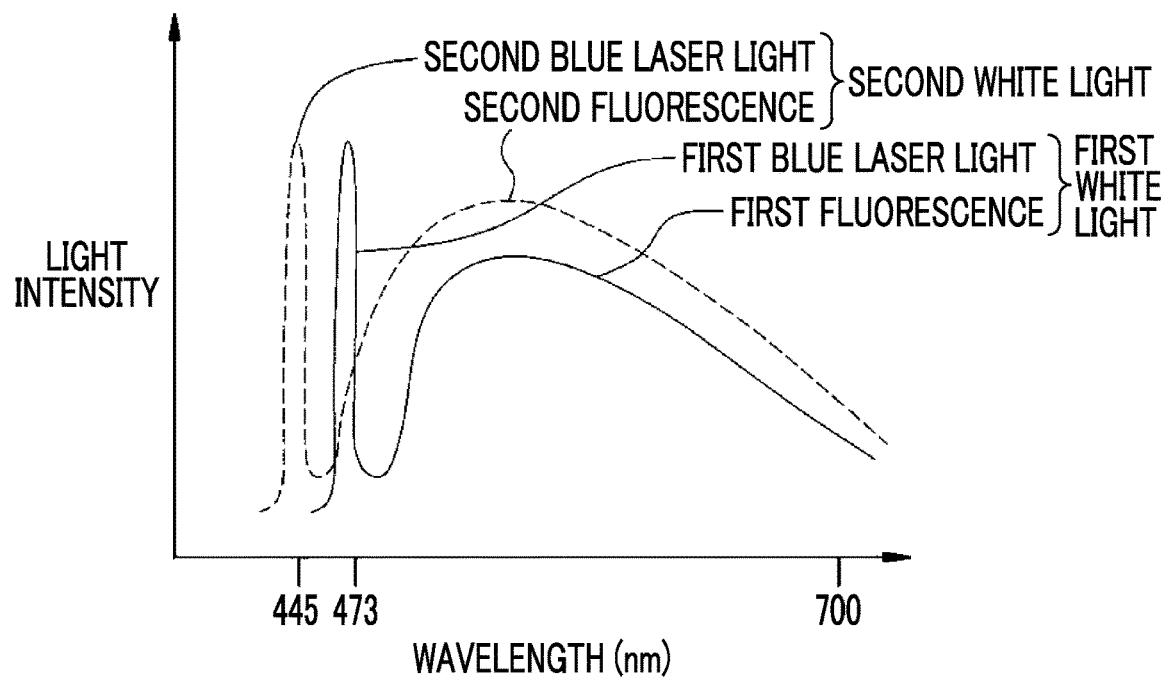
FIG. 22 is a graph showing the spectrum of light emitted in the oxygen saturation observation mode.

On the other hand, in the oxygen saturation observation mode, the first blue laser light and the second blue laser light are alternately incident on the phosphor 206. Therefore, the observation target is alternately illuminated with the first white light and the second white light having the spectrums shown in FIG. 22. The first white light is configured to include first blue laser light and first fluorescence of green to red that is excited and emitted from the phosphor 206 by the first blue laser light. Accordingly, the wavelength range of the first white light is the entire visible light region. The second white light is the same as the second white light emitted in the normal observation mode.

The light source control unit 22 controls each light source so as to switch the first white light and the second white light. The light source control unit 22 outputs a synchronization signal to an imaging control unit (not shown) that controls the image sensor 38, thereby controlling synchronization between the emission timing of illumination light and a frame in which imaging is performed by the image sensor 38 or the output of an image from the image sensor 38. Therefore, the image sensor 38 outputs an image of each color of BGR corresponding to each illumination light beam from the pixel of each color for each frame.

In the first frame, the light source control unit 22 turns on the first blue laser light source 202 to illuminate the observation target using the first white light including the first blue laser light and the first fluorescence. The image sensor 38 receives the first blue laser light at the B pixel and outputs the B1 image, receives a component in a wavelength range corresponding to the green light G included in the first fluorescence at the G pixel and outputs the G image, and receives a component in a wavelength range corresponding to the red light R included in the first fluorescence at the R pixel and outputs the R image.

In the second frame, the light source control unit 22 turns on the second blue laser light source 204 to illuminate the observation target using the second white light including the second blue laser light and the second fluorescence. The image sensor 38 receives the second blue laser light at the B pixel and outputs the B2 image, receives a component in a wavelength range corresponding to the green light G included in the second fluorescence at the G pixel and outputs the G image, and receives a component in a wavelength range corresponding to the red light R included in the second fluorescence at the R pixel and outputs the R image.

In the fifth embodiment, the B1 image, the B2 image, the G image, and the R image obtained at the time of pre-imaging are the correction image 86. The B1 image, the B2 image, the G image, and the R image obtained at the time of main imaging are the oxygen saturation calculation image 76. Based on these images, the calculation of the oxygen saturation correction amount, the calculation of the oxygen saturation, the correction of the oxygen saturation, and the generation of the oxygen saturation image are performed in the same manner as in the first embodiment described above. Then, the storage unit 92 stores the correction image 86 and the oxygen saturation image 96 so as to be associated with each other. The same method as in any one of the second to fourth embodiments may be used without being limited to the same method as in the first embodiment.

Sixth Embodiment

In a sixth embodiment, the observation target is illuminated using a broadband light source, such as a xenon lamp, and a rotary filter instead of the four LEDs 20a to 20d shown in the first embodiment described above. In addition, the observation target is imaged using a monochrome image sensor instead of the color image sensor 38. Others are the same as in the first embodiment.

Figure 23:
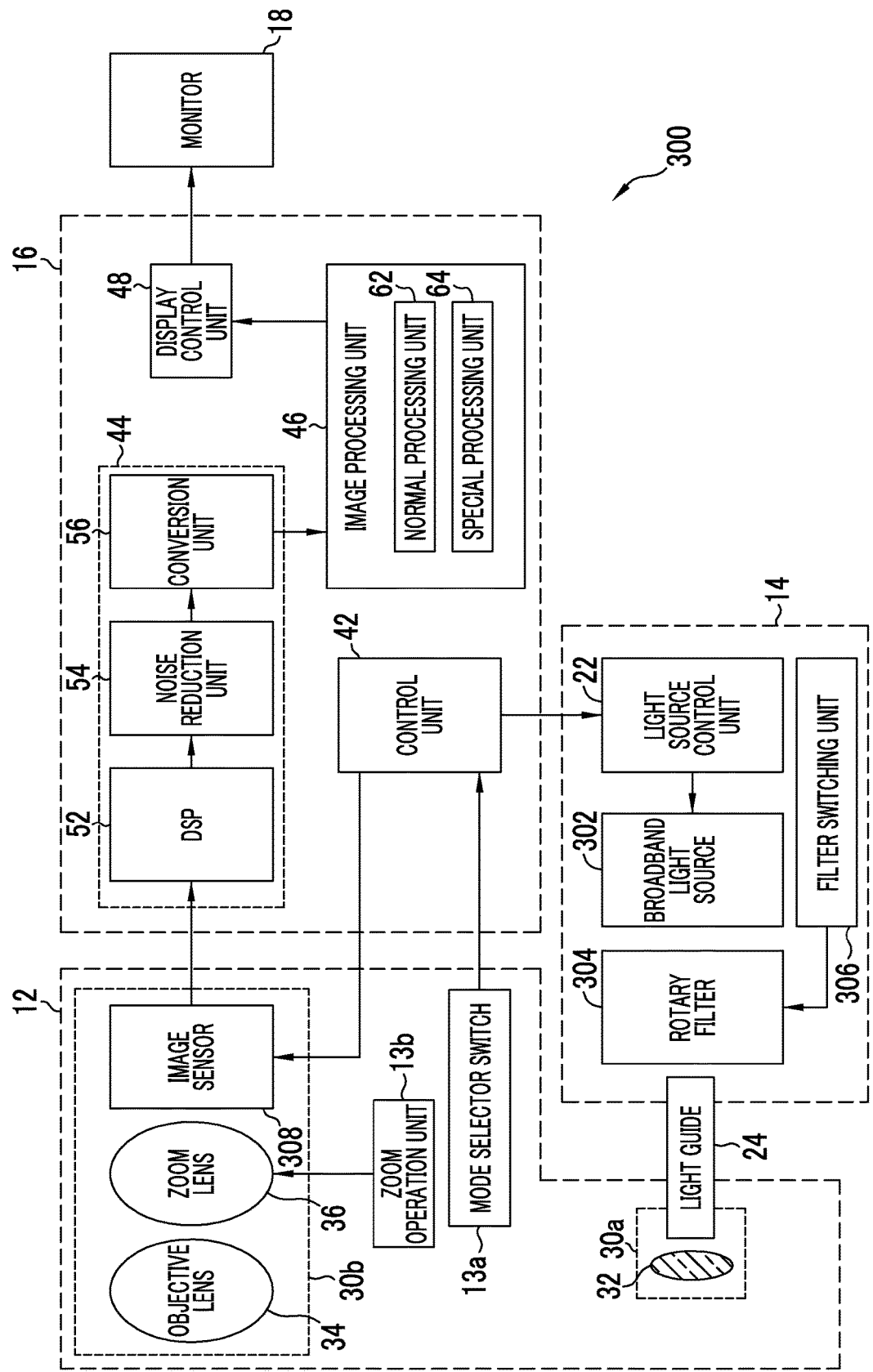
FIG. 23 is a block diagram of an endoscope system of a sixth embodiment.

As shown in FIG. 23, in an endoscope system 300, the light source device 14 includes a broadband light source 302, a rotary filter 304, and a filter switching unit 306 instead of the four LEDs 20a to 20d provided in the endoscope system 10 of the first embodiment. In addition, instead of the color image sensor 38, a monochrome image sensor 308 in which no color filter is provided is provided in the imaging optical system 30b.

The broadband light source 302 is a white LED, a xenon lamp, or the like, and emits white light having a wavelength range from blue to red. The rotary filter 304 has an inner filter 310 on the inner side and an outer filter 312 on the outer side (refer to FIG. 24).

The filter switching unit 306 is electrically connected to the light source control unit 22, and moves the rotary filter 304 in the radial direction according to the observation mode. In the case of the normal observation mode, the filter switching unit 306 inserts the inner filter 310 of the rotary filter 304 in the optical path of white light. On the other hand, in the case of the oxygen saturation observation mode, the filter switching unit 306 inserts the outer filter 312 in the optical path of white light.

Figure 24:
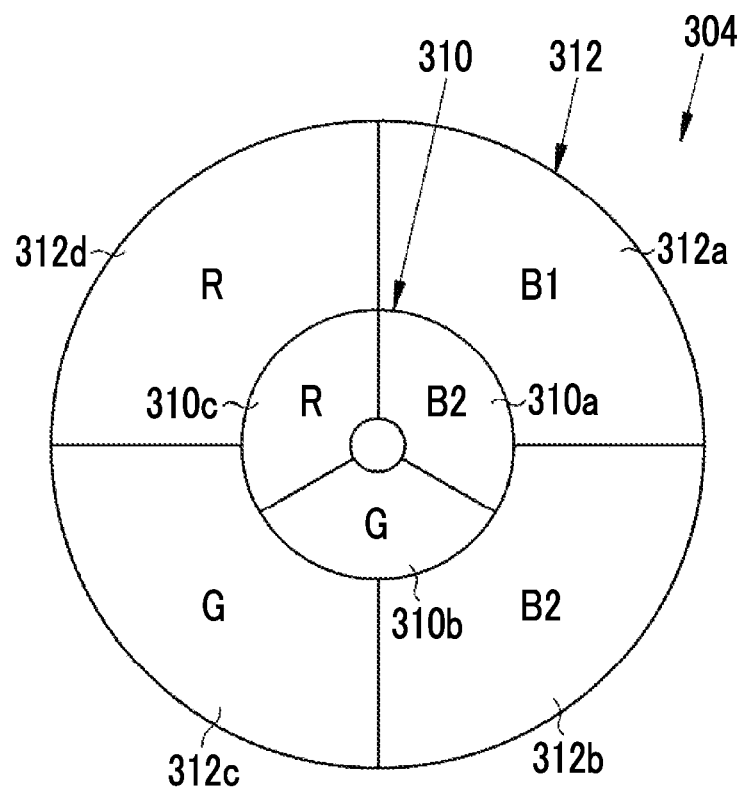
FIG. 24 is a plan view showing a rotary filter.

As shown in FIG. 24, in the inner filter 310, a B2 filter 310a that transmits B2 light of the white light, a G filter 310b that transmits G light of the white light, and an R filter 310c that transmits R light of the white light are provided along the circumferential direction. Therefore, in the normal observation mode, the rotary filter 304 rotates to sequentially illuminate the observation target with the B2 light, the G light, and the R light.

In the outer filter 312, a B1 filter 312a that transmits B1 light of the white light, a B2 filter 312b that transmits B2 light of the white light, a G filter 312c that transmits G light of the white light, and an R filter 312d that transmits R light of the white light are provided along the circumferential direction. Therefore, in the oxygen saturation observation mode, the rotary filter 304 rotates in a state in which the outer filter 312 is inserted in the optical path of the white light, so that the observation target is sequentially illuminated with the B1 light, the B2 light, the G light, and the R light.

In the endoscope system 300, in the case of the normal observation mode, the observation target is imaged by the monochrome image sensor 308 every time the observation target is illuminated with the B2 light, the G light, and the R light. As a result, a B image, a G image, and an R image are obtained. Then, based on the images of the three colors, a normal image is generated using the same method as in the first embodiment described above.

On the other hand, in the case of the oxygen saturation observation mode, at the time of pre-imaging, the observation target is imaged by the monochrome image sensor 308 every time the observation target is sequentially illuminated with the B1 light, the B2 light, the G light, and the R light. The B1 image, the B2 image, the G image, and the R image obtained as a result are the correction image 86. In addition, at the time of main imaging, the observation target is imaged by the monochrome image sensor 308 every time the observation target is sequentially illuminated with the B1 light, the B2 light, the G light, and the R light. The B1 image, the B2 image, the G image, and the R image obtained as a result are the oxygen saturation calculation image 76. Based on these images, the calculation of the oxygen saturation correction amount, the calculation of the oxygen saturation, the correction of the oxygen saturation, and the generation of the oxygen saturation image are performed in the same manner as in the first embodiment described above. Then, the storage unit 92 stores the correction image 86 and the oxygen saturation image 96 so as to be associated with each other. The same method as in any one of the second to fourth embodiments may be used without being limited to the same method as in the first embodiment.

Seventh Embodiment

Figure 25:
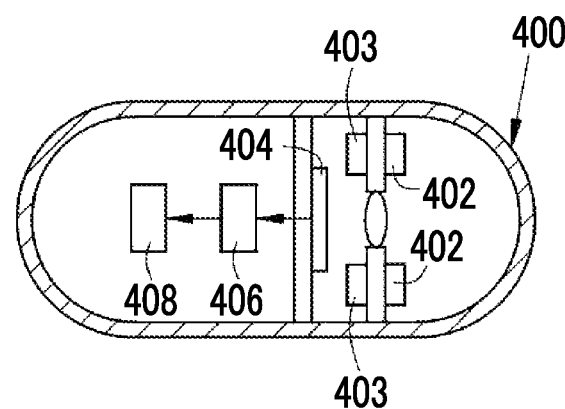
FIG. 25 is a schematic diagram of a capsule endoscope of a seventh embodiment.

In the first to sixth embodiments described above, the present invention is implemented by the endoscope system in which the endoscope 12 including an image sensor is inserted into the subject to observe the inside of the subject. However, the present invention is also suitable for a capsule endoscope system. For example, as shown in FIG. 25, a capsule endoscope system includes at least a capsule endoscope 400 and a processor device (not shown).

The capsule endoscope 400 includes a light source 402, a control unit 403, an image sensor 404, an image processing unit 406, and a transmitting and receiving antenna 408. The light source 402 corresponds to the light source unit 20. The control unit 403 functions similar to the light source control unit 22 and the control unit 42. In addition, the control unit 403 can perform radio communication with the processor device of the capsule endoscope system through the transmitting and receiving antenna 408. Although the processor device of the capsule endoscope system is almost the same as the processor device 16 of each of the first to sixth embodiments described above, the image processing unit 406 corresponding to the image acquisition unit 44 and the image processing unit 46 is provided in the capsule endoscope 400, and the generated oxygen saturation image and the like are transmitted to the processor device through the transmitting and receiving antenna 408. The image sensor 404 is configured similar to the image sensor 38.

In each of the embodiments described above, the oxygen saturation as the functional biometric feature amount has been described as an example of the biometric feature amount. However, the present invention can also be applied to blood vessel information without being limited to the oxygen saturation. The blood vessel information is, for example, the number of blood vessels, the number of branches, a branching angle, a distance between branch points, the number of crossings, a thickness, a change in thickness, complexity of thickness change, a length, an interval, a depth with respect to a mucous membrane as a reference, a height difference, an inclination, an area, a density, a contrast, a color, color change, degree of meandering, blood concentration, proportion of arteries, proportion of veins, concentration of administered coloring agent, a traveling pattern, or a blood flow rate. The blood vessel information is included in the morphological biometric feature amount. The above-described blood vessel information is an example, and information regarding other blood vessels may be calculated as blood vessel information.

The blood vessel information may differ depending on various parts such as esophagus, stomach, and large intestine, individual differences among patients such as sex and age, and the like. In order to accurately calculate the blood vessel information, it is necessary to correct the influence due to the individual difference and the like by performing pre-imaging before actually calculating the blood vessel information, in the same manner as in the correction of the oxygen saturation. Therefore, in the case of calculating the blood vessel information instead of the oxygen saturation, similar to the correction of the oxygen saturation, a correction amount for correcting the value of the blood vessel information is calculated using the correction image obtained by pre-imaging, and the value of the blood vessel information is corrected according to the correction amount.

In this case, the special processing unit has a configuration in which the correlation storage unit 72 is deleted and "oxygen saturation" is replaced with "blood vessel information", for example, in FIG. 3. The processing content is processing in which "oxygen saturation" is replaced with "blood vessel information" and step S17 is deleted in FIG. 7. Alternatively, the special processing unit may have a configuration in which the correlation storage unit 72 is deleted and "oxygen saturation" is replaced with "blood vessel information" in FIG. 16. In this case, the processing content is processing in which "oxygen saturation" is replaced with "blood vessel information" and step S17 is deleted in FIG. 17.

The number of blood vessels is the number of blood vessels in the entire image or a region of interest (ROI). The number of blood vessels is calculated using, for example, the number of branch points (the number of branches) of the blood vessel, the number of intersections (the number of crossings) with other blood vessels, and the like. The branching angle of a blood vessel is an angle formed by two blood vessels at a branch point. The distance between branch points is a linear distance between any branch point and a branch point adjacent thereto or a length along a blood vessel from any branch point to a branch point adjacent thereto. The region of interest can be designated by a pointing device, a keyboard, or the like.

The number of crossings between blood vessels is the number of intersections at which blood vessels having different submucosal depths cross each other on the image. More specifically, the number of crossings between blood vessels is the number of blood vessels, which are located at relatively shallow submucosal positions, crossing blood vessels located at deep positions.

The thickness of a blood vessel (blood vessel diameter) is a distance between the blood vessel and the boundary of the mucous membrane. For example, the thickness of a blood vessel (blood vessel diameter) is a value obtained by counting the number of pixels along the lateral direction of the blood vessel from the edge of the blood vessel through the blood vessel. Therefore, the thickness of a blood vessel is the number of pixels. However, in a case where the imaging distance, zoom magnification and the like at the time of capturing an image are known, the number of pixels can be converted into a unit of length, such as "μm", as necessary.

The change in the thickness of a blood vessel is blood vessel information regarding a variation in the thickness of the blood vessel, and is also referred to as the aperture inconsistency. The change in the thickness of a blood vessel is, for example, a change rate of the blood vessel diameter (also referred to as the degree of expansion). Using the thickness (minimum diameter) of the thinnest portion of the blood vessel and the thickness (maximum diameter) of the thickest portion of the blood vessel, the change rate of the blood vessel diameter is calculated as "blood vessel diameter change rate (%)=minimum diameter/maximum diameter×100".

In a case where an image obtained by imaging the observation target in a past examination and an image obtained by imaging the same observation target in a subsequent new examination are used, a temporal change in the thickness of the same blood vessel in the image obtained by the subsequent new examination with respect to the thickness of the blood vessel in the image obtained by the past examination may be the change in the thickness of the blood vessel.

As a change in the thickness of the blood vessel, a proportion of a small diameter portion or a proportion of a large diameter portion may be calculated. The small diameter portion is a portion whose thickness is equal to or less than the threshold value, and the large diameter portion is a portion where the thickness is equal to or greater than the threshold value. The proportion of a small diameter portion is calculated as "proportion of small diameter portion (%)=length of small diameter portion/length of blood vessel×100". Similarly, the proportion of a large diameter portion is calculated as "proportion of large diameter portion (%)=length of large diameter portion/length of blood vessel×100".

The complexity of the change in the thickness of a blood vessel (hereinafter, referred to as the "complexity of the thickness change") is blood vessel information indicating how complex the change is in a case where the thickness of the blood vessel changes, and is blood vessel information calculated by combining a plurality of pieces of blood vessel information indicating the change in the thickness of the blood vessel (that is, the change rate of the blood vessel diameter, the proportion of the small diameter portion, or the proportion of the large diameter portion). The complexity of the thickness change can be calculated, for example, by the product of the change rate of the blood vessel diameter and the proportion of the small diameter portion.

The length of the blood vessel is the number of pixels obtained by counting the blood vessel along the longitudinal direction.

The interval between blood vessels is the number of pixels showing the mucous membrane between the edges of the blood vessel. In the case of one blood vessel, the interval between blood vessels has no value.

The depth of a blood vessel is measured with the mucous membrane (more specifically, the mucosal surface) as a reference. The depth of a blood vessel with the mucous membrane as a reference can be calculated based on, for example, the color of the blood vessel.

The height difference of a blood vessel is the magnitude of the difference in the depth of the blood vessel. For example, the height difference of one blood vessel of interest is calculated by the difference between the depth (maximum depth) of the deepest portion of the blood vessel and the depth (minimum depth) of the shallowest portion. In a case where the depth is constant, the height difference is zero.

The inclination of a blood vessel is the change rate of the depth of the blood vessel, and is calculated using the length of the blood vessel and the depth of the blood vessel. That is, the inclination of a blood vessel is calculated as "inclination of blood vessel=depth of blood vessel/length of blood vessel". The blood vessel may be divided into a plurality of sections, and the inclination of the blood vessel may be calculated in each section.

The area of a blood vessel is the number of pixels showing a blood vessel or a value proportional to the number of pixels showing a blood vessel. The area of a blood vessel is calculated within the region of interest, outside the region of interest, or for the entire image.

The density of blood vessels is a proportion of blood vessels in a unit area. A region of a specific size (for example, a region of a unit area) including pixels for calculating the density of blood vessels at its approximate center is cut out, and the proportion of blood vessels occupying all the pixels within the region is calculated. By performing this on all the pixels of the region of interest or the entire image, the density of blood vessels of each pixel can be calculated.

The contrast of a blood vessel is a relative contrast with respect to the mucous membrane of the observation target. The contrast of a blood vessel is calculated as, for example, "$Y_V/Y_M$" or "$(Y_V-Y_M)/(Y_V+Y_M)$", using the brightness $Y_V$ of the blood vessel and the brightness $Y_M$ of the mucous membrane.

The color of a blood vessel is each value of RGB of pixels showing the blood vessel. The change in the color of a blood vessel is a difference or ratio between the maximum value and the minimum value of the RGB values of pixels showing the blood vessel. For example, the ratio between the maximum value and the minimum value of the B value of a pixel showing the blood vessel, the ratio between the maximum value and the minimum value of the G value of a pixel showing the blood vessel, or the ratio between the maximum value and the minimum value of the R value of a pixel showing the blood vessel indicates a change in the color of the blood vessel. Needless to say, conversion into complementary colors may be performed to calculate the color of the blood vessel and a change in the color of the blood vessel for each value of cyan, magenta, yellow, green, and the like.

The degree of meandering of a blood vessel is blood vessel information indicating the size of a range in which the blood vessel travels while meandering. The degree of meandering of a blood vessel is, for example, the area (the number of pixels) of a minimum rectangle including the blood vessel for which the degree of meandering is to be calculated. The ratio of the length of the blood vessel to the linear distance between the start point and the end point of the blood vessel may be used as the degree of meandering of the blood vessel.

The blood concentration of a blood vessel is blood vessel information proportional to the amount of hemoglobin contained in a blood vessel. Since the ratio (G/R) of the G value to the R value of a pixel showing a blood vessel is proportional to the amount of hemoglobin, the blood concentration can be calculated for each pixel by calculating the value of G/R.

The proportion of arteries is the ratio of the number of pixels of arteries to the number of pixels of all the blood vessels. Similarly, the proportion of veins is the ratio of the number of pixels of veins to the number of pixels of all the blood vessels. Arteries and veins can be distinguished by oxygen saturation. For example, assuming that a blood vessel having an oxygen saturation of 70% or more is an artery and a blood vessel having an oxygen saturation less than 70% is a vein, blood vessels can be divided into arteries and veins. Therefore, the proportion of arteries and the proportion of veins can be calculated.

The concentration of an administered coloring agent is the concentration of a coloring agent sprayed on the observation target or the concentration of a coloring agent injected into the blood vessel by intravenous injection. The concentration of the administered coloring agent is calculated, for example, by the ratio of the pixel value of the coloring agent color to the pixel value of a pixel other than the coloring agent color. For example, in a case where a coloring agent for coloring in blue is administered, B/G, B/R, and the like indicate the concentration of the coloring agent fixed (or temporarily adhered) to the observation target.

The traveling pattern of a blood vessel is blood vessel information regarding the traveling direction of a blood vessel. The traveling pattern of a blood vessel is, for example, an average angle (traveling direction) of a blood vessel with respect to a reference line randomly set, a dispersion (variation in traveling direction) of an angle formed by a blood vessel with respect to a reference line set randomly, and the like.

The blood flow rate (also referred to as a blood flow speed) of a blood vessel is the number of red blood cells that can pass per unit time. In a case where an ultrasound probe is used together through the forceps channel of the endoscope 12 or the like, the Doppler shift frequency of each pixel showing the blood vessel of the image can be calculated by using the signal obtained by the ultrasound probe. The blood flow rate of the blood vessel can be calculated by using the Doppler shift frequency.

EXPLANATION OF REFERENCES 10, 200, 300: endoscope system
16: processor device
18: monitor 44: image acquisition unit
46: image processing unit
64, 114, 124, 134: special processing unit
71: calculation value calculation unit
72: correlation storage unit
73: oxygen saturation calculation unit
74: oxygen saturation image generation unit
75, 138: LUT
82: oxygen saturation correction amount calculation unit
84: oxygen saturation correction unit
92: storage unit
116: region setting unit
126: image correction amount calculation unit
128: image correction unit
136: table calibration unit

What is claimed is:

1. An endoscope system, comprising:
a processor with a memory, configured to:
  calculate a biometric feature amount of an actual observation target using a plurality of biometric feature amount calculation images obtained by imaging the actual observation target with a plurality of illumination light beams having different wavelength ranges;
acquire a reference image by imaging a normal part of an ideal observation target, and a correction image obtained by imaging the actual observation target;
calculate an image correction amount for the biometric feature amount calculation image according to a difference between the actual correction image and the reference image;
correct the biometric feature amount calculation image according to the image correction amount; and
store the correction image and a first biometric feature amount image, which shows the biometric feature amount using the biometric feature amount calculation image after correction, so as to be associated with each other,
wherein the memory stores a plurality of sets of the correction images, and
in response to determining that the correction image used for calculation of the image correction amount is acquired under non-appropriate imaging conditions, the processor calculates the image correction amount by changing a set of the correction images, and corrects the biometric feature amount calculation image using the image correction amount calculated by changing the set of the correction images.

2. The endoscope system according to claim 1,
wherein the biometric feature amount is a morphological biometric feature amount or a functional biometric feature amount.

3. The endoscope system according to claim 2,
wherein the morphological biometric feature amount is blood vessel information, and the functional biometric feature amount is an oxygen saturation.

4. The endoscope system according to claim 1,
wherein the memory stores, in addition to the first biometric feature amount image, any of the biometric feature amount calculation image after correction, the biometric feature amount calculation image before correction, the image correction amount, and the biometric feature amount using the biometric feature amount calculation image after correction so as to be associated with the correction image.

5. The endoscope system according to claim 1, further comprising:
a display that displays the correction image and the first biometric feature amount image.

6. The endoscope system according to claim 1,
wherein the processor is further configured to:
  set a usable region for the correction image stored in the memory,
  calculate the image correction amount using the usable region in a case where the processor sets the usable region, and
  correct the biometric feature amount calculation image using the image correction amount using the usable region.

7. The endoscope system according to claim 6,
wherein the processor sets a region other than an unused region as the usable region by setting the unused region for the correction image.

8. The endoscope system according to claim 1,
wherein, in response to determining that the correction image used for calculation of the image correction amount is acquired under non-appropriate imaging conditions, the processor acquires a new correction image, calculates the image correction amount using the new correction image, and corrects the biometric feature amount calculation image using the image correction amount using the new correction image.

9. The endoscope system according to claim 1,
wherein, between a case where the processor acquires the correction image and the biometric feature amount calculation image in real time during observation of the actual observation target and a case where the processor acquires the correction image and the biometric feature amount calculation image after completion of observation of the actual observation target, the processor changes calculation accuracy of the image correction amount, and changes correction accuracy of the biometric feature amount calculation image.

10. The endoscope system according to claim 9,
wherein calculation accuracy of the image correction amount and correction accuracy of the biometric feature amount calculation image in a case where the processor acquires the correction image and the biometric feature amount calculation image after completion of observation of the actual observation target are higher than calculation accuracy of the image correction amount and correction accuracy of the biometric feature amount calculation image in a case where the processor acquires the correction image and the biometric feature amount calculation image in real time during observation of the actual observation target.

11. The endoscope system according to claim 1,
wherein the processor acquires the correction image, which is obtained by imaging the actual observation target, before calculating the biometric feature amount.

12. The endoscope system according to claim 1,
wherein the processor is further configured to calibrate a look-up table for associating pixel values of the biometric feature amount calculation images with the biometric feature amount of the actual observation target using the correction image; and
the memory stores a second biometric feature amount image, which shows the biometric feature amount using the look-up table after calibration, so as to be associated with each other,
the processor is further configured to calculate the biometric feature amount of an actual observation target using a plurality of the biometric feature amount calculation images and the look-up table, and the memory stores the correction image and the second biometric feature amount image so that the compression ratio of the correction image is lower than the compression ratio of the second biometric feature amount image associated the correction image.

13. An endoscope system, comprising:
a processor with a memory, configured to:
calculate a biometric feature amount of an actual observation target using a plurality of biometric feature amount calculation images obtained by imaging the actual observation target with a plurality of illumination light beams having different wavelength ranges;
acquire a reference image by imaging a normal part of an ideal observation target, and a correction image obtained by imaging the actual observation target;
calculate an image correction amount for the biometric feature amount calculation image according to a difference between the actual correction image and the reference image;
correct the biometric feature amount calculation image according to the image correction amount;
store the correction image and a first biometric feature amount image, which shows the biometric feature amount using the biometric feature amount calculation image after correction, so as to be associated with each other, and store the correction image and a second biometric feature amount image, which shows the biometric feature amount calculated using the look-up table after calibration, so as to be associated with each other; and
a display that displays the correction image and the first biometric feature amount image;
wherein the processor is further configured to set a usable region for the correction image stored in the memory,
the memory stores a plurality of sets of the correction images,
in response to determining that the correction image used for calculation of the image correction amount is acquired under non-appropriate imaging conditions, the processor calculates the image correction amount by changing a set of the correction images, and corrects the biometric feature amount calculation image using the image correction amount calculated by changing the set of the correction images,
the biometric feature amount is blood vessel information or an oxygen saturation,
the memory stores, in addition to the first biometric feature amount image, any of the biometric feature amount calculation image after correction, the biometric feature amount calculation image before correction, the image correction amount, and the biometric feature amount using the biometric feature amount calculation image after correction so as to be associated with the correction image,
the processor is further configured to:
calculate the image correction amount using the usable region in a case where the processor sets the usable region,
correct the biometric feature amount calculation image using the image correction amount using the usable region,
set a region other than an unused region as the usable region by setting the unused region for the correction image,
in response to determining that the correction image used for calculation of the image correction amount is acquired under non-appropriate imaging conditions, the processor acquires a new correction image, calculates the image correction amount using the new correction image, and corrects the biometric feature amount calculation image using the image correction amount using the new correction image,
between a case where the processor acquires the correction image and the biometric feature amount calculation image in real time during observation of the actual observation target and a case where the processor acquires the correction image and the biometric feature amount calculation image after completion of observation of the actual observation target, changes calculation accuracy of the image correction amount, and changes correction accuracy of the biometric feature amount calculation image,
calculation accuracy of the image correction amount and correction accuracy of the biometric feature amount calculation image in a case where the processor acquires the correction image and the biometric feature amount calculation image after completion of observation of the actual observation target are higher than calculation accuracy of the image correction amount and correction accuracy of the biometric feature amount calculation image in a case where the processor acquires the correction image and the biometric feature amount calculation image in real time during observation of the actual observation target,
the processor is further configured to calculate the biometric feature amount of an observation target using a plurality of the biometric feature amount calculation images and the look-up table, and
the memory stores the correction image and the second biometric feature amount image so that the compression ratio of the correction image is lower than the compression ratio of the second biometric feature amount image associated the correction image.

14. A processor device, comprising:
a processor with a memory, configured to:
calculate a biometric feature amount of an actual observation target using a plurality of biometric feature amount calculation images obtained by imaging the actual observation target with a plurality of illumination light beams having different wavelength ranges;
acquire a reference image by imaging a normal part of an ideal observation target, and a correction image obtained by imaging the actual observation target;
calculate an image correction amount for the biometric feature amount calculation image according to a difference between the actual correction image and the reference image;
correct the biometric feature amount calculation image according to the image correction amount; and
store the correction image and a first biometric feature amount image, which shows the biometric feature amount using the biometric feature amount calculation image after correction, so as to be associated with each other,
wherein the memory stores a plurality of sets of the correction images, and
in response to determining that the correction image used for calculation of the image correction amount is acquired under non-appropriate imaging conditions, the processor calculates the image correction amount by changing a set of the correction images, and corrects the biometric feature amount calculation image using the image correction amount calculated by changing the set of the correction images.

15. An operation method of an endoscope system having a processor with a memory, the processor configured to calculate a biometric feature amount of an actual observation target using a plurality of biometric feature amount calculation images obtained by imaging the actual observation target with a plurality of illumination light beams having different wavelength ranges, the method comprising:
- a step in which the processor acquires a correction image obtained by imaging the actual observation target;
- a step in which the processor calculates an image correction amount for the biometric feature amount calculation image using the correction image;
- a step in which the processor corrects the biometric feature amount calculation image according to the image correction amount;
- a step in which the processor calculates the biometric feature amount using the biometric feature amount calculation image after correction;
- a step in which the memory stores the correction image and a first biometric feature amount image, which shows the biometric feature amount using the biometric feature amount calculation image after correction, so as to be associated with each other;
- a step in which the memory stores a plurality of sets of the correction images; and
- a step in which, in response to determining that the correction image used for calculation of the image correction amount is acquired under non-appropriate imaging conditions, the processor calculates the image correction amount by changing a set of the correction images, and corrects the biometric feature amount calculation image using the image correction amount calculated by changing the set of the correction images.

* * * * *